US012558004B2

(12) United States Patent
Aroyan et al.

(10) Patent No.: US 12,558,004 B2
(45) Date of Patent: Feb. 24, 2026

(54) SENSOR DEVICE MONITORS FOR CALIBRATION

(71) Applicant: Medtronic MiniMed, Inc., Northridge, CA (US)

(72) Inventors: Sarkis D. Aroyan, Northridge, CA (US); Ellis Garai, Northridge, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 862 days.

(21) Appl. No.: 17/454,751

(22) Filed: Nov. 12, 2021

(65) Prior Publication Data

US 2023/0148916 A1    May 18, 2023

(51) Int. Cl.
*A61B 5/145* (2006.01)
*A61B 5/00* (2006.01)
*A61M 5/172* (2006.01)

(52) U.S. Cl.
CPC ........ *A61B 5/14532* (2013.01); *A61B 5/0004* (2013.01); *A61M 5/1723* (2013.01); *A61M 2005/1726* (2013.01)

(58) Field of Classification Search
CPC .............. A61B 5/14532; A61B 5/0004; A61B 5/14865; A61B 5/1495; A61M 5/1723; A61M 2005/1726
See application file for complete search history.

(56) References Cited

U.S. PATENT DOCUMENTS 6,175,752 B1 * 1/2001 Say ...................... A61B 5/1495
                                                            128/903
8,423,114 B2    4/2013 Simpson et al.

10,660,555 B2    5/2020 Wang et al.
10,908,114 B2 * 2/2021 Estes ..................... G01N 27/403
2009/0242399 A1 * 10/2009 Kamath ............. A61B 5/14532
                                                            204/406

(Continued)

FOREIGN PATENT DOCUMENTS

WO    2010099507 A1    9/2010
WO    2023086232 A1    5/2023

OTHER PUBLICATIONS

International Search Report and Written Opinion dated Apr. 28, 2023, in Application No. PCT/US2022/048417 [MEDTP124].

*Primary Examiner* — Devin B Henson
*Assistant Examiner* — Erin Kathleen Mccormack
(74) *Attorney, Agent, or Firm* — Weaver Austin Villeneuve & Sampson LLP

(57) ABSTRACT

A system for monitoring glucose includes processing circuitry and a glucose monitor comprising one or more monitor electrodes and one or more working electrodes, wherein a first chemistry stack is disposed on at least one of the monitor electrode(s) and a second chemistry stack is disposed on at least one of the working electrode(s) is described herein. The processing circuitry may be configured to measure one or more calibration values of an operating parameter of the monitor electrode(s), retrieve one or more pre-calibration values of the operating parameter of the monitor electrode(s), wherein the pre-calibration value(s) were measured before the calibration value, determine one or more delta values using the calibration value(s) and the pre-calibration value(s), and calibrate glucose values sensed by the working electrode(s) using the delta value(s).

20 Claims, 7 Drawing Sheets

(56)  References Cited

U.S. PATENT DOCUMENTS

| | | | |
|---|---|---|---|
| 2013/0158376 A1* | 6/2013 | Hayter | A61B 5/14503 |
| | | | 600/347 |
| 2017/0188907 A1* | 7/2017 | Ma | G01N 33/66 |
| 2018/0070866 A1 | 3/2018 | Raahemifar et al. | |
| 2019/0076070 A1 | 3/2019 | Nogueira et al. | |
| 2019/0150803 A1 | 5/2019 | Vanslyke et al. | |
| 2019/0150809 A1 | 5/2019 | Ouyang et al. | |
| 2019/0175080 A1 | 6/2019 | Varsavsky et al. | |
| 2019/0223766 A1 | 7/2019 | Harley-Trochimczyk et al. | |
| 2020/0029871 A1 | 1/2020 | Hayter et al. | |
| 2020/0275894 A1 | 9/2020 | Burnette et al. | |
| 2021/0022676 A1 | 1/2021 | Lamego et al. | |
| 2021/0068720 A1* | 3/2021 | Böhm | A61B 5/157 |
| 2021/0231602 A1* | 7/2021 | Estes | A61B 5/14865 |
| 2021/0345914 A1* | 11/2021 | Moein | A61B 5/14532 |
| 2024/0324912 A1* | 10/2024 | Yang | A61B 5/14532 |

* cited by examiner

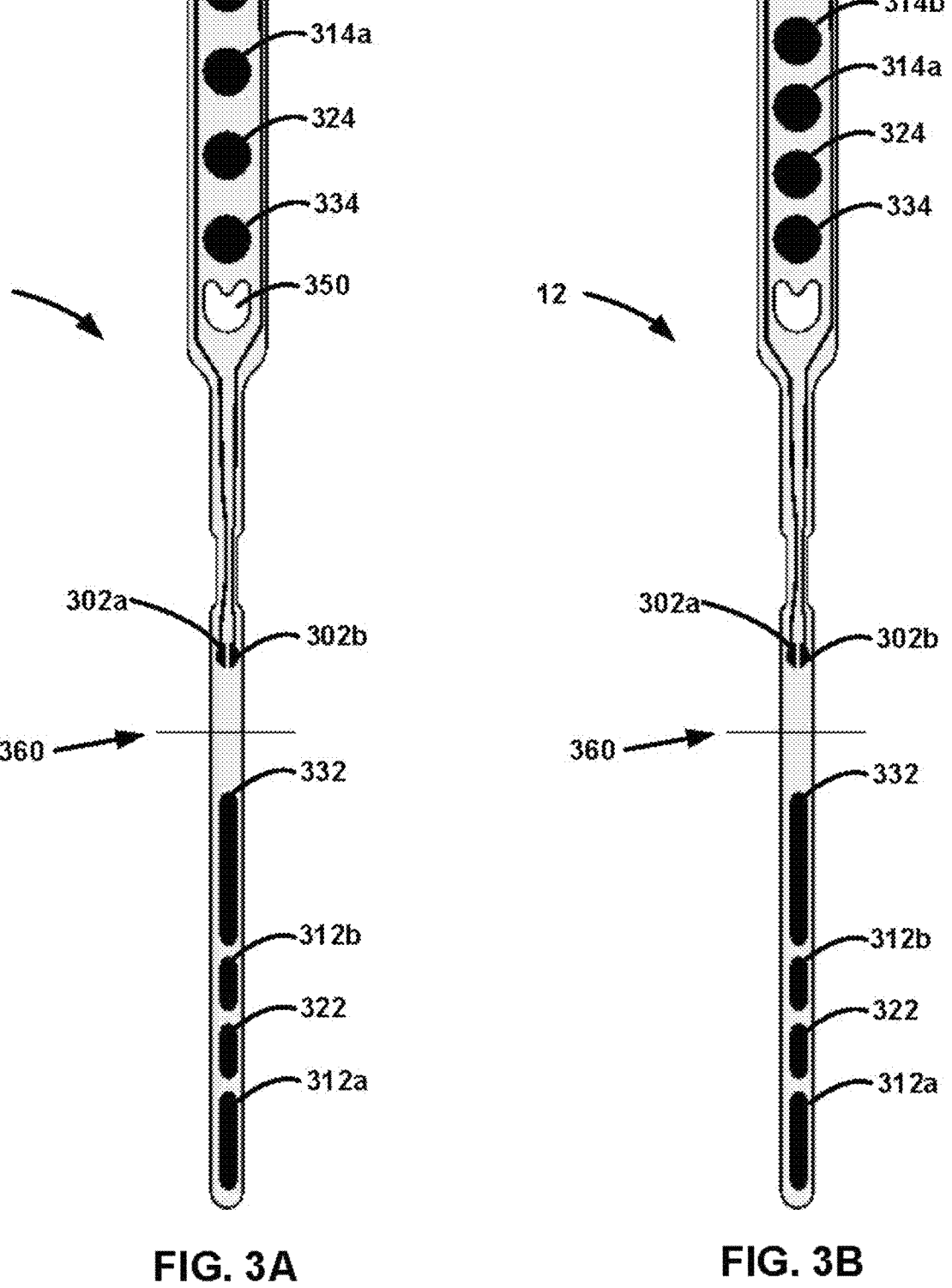
FIG. 3A                   FIG. 3B

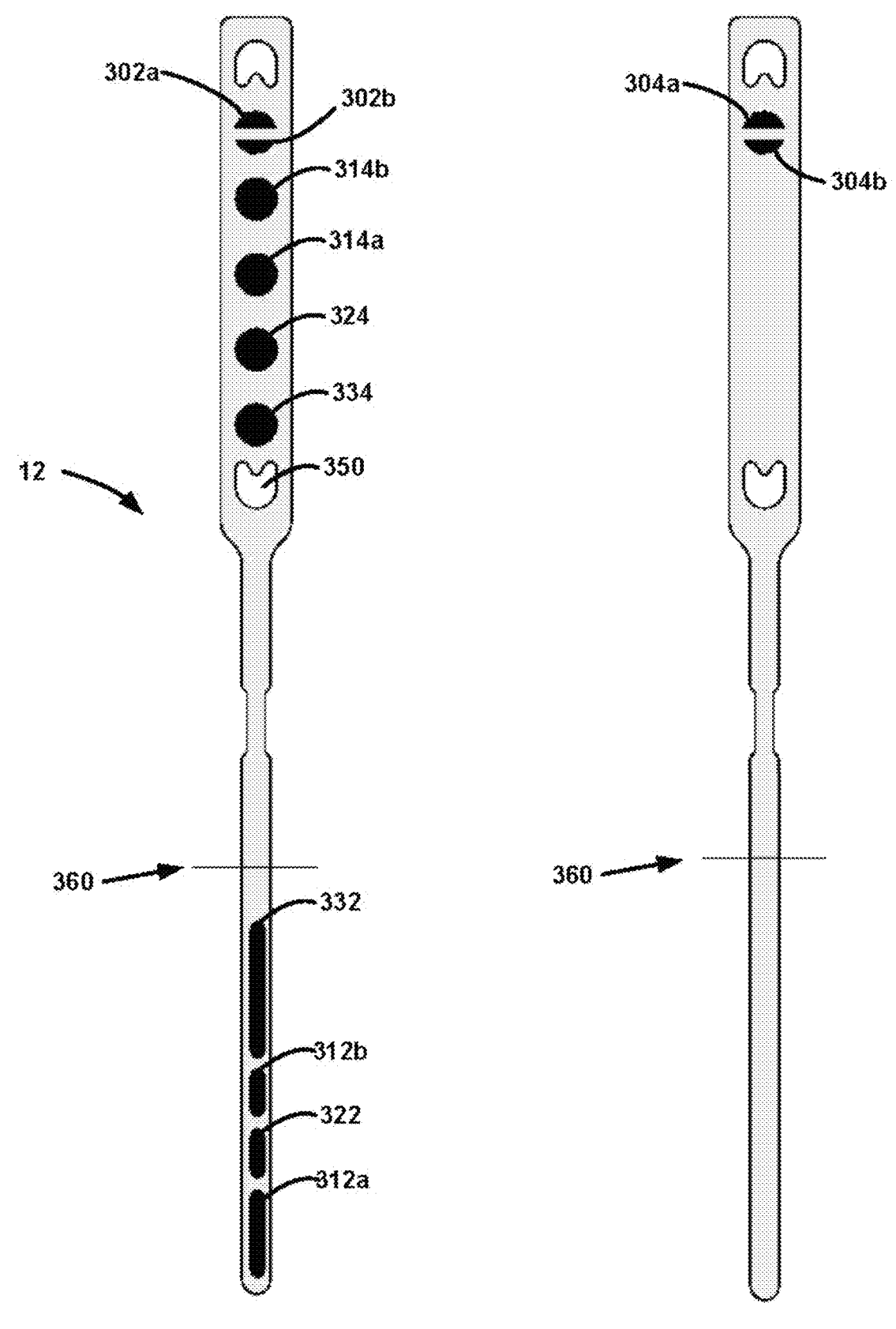
FIG. 4A                        FIG. 4B

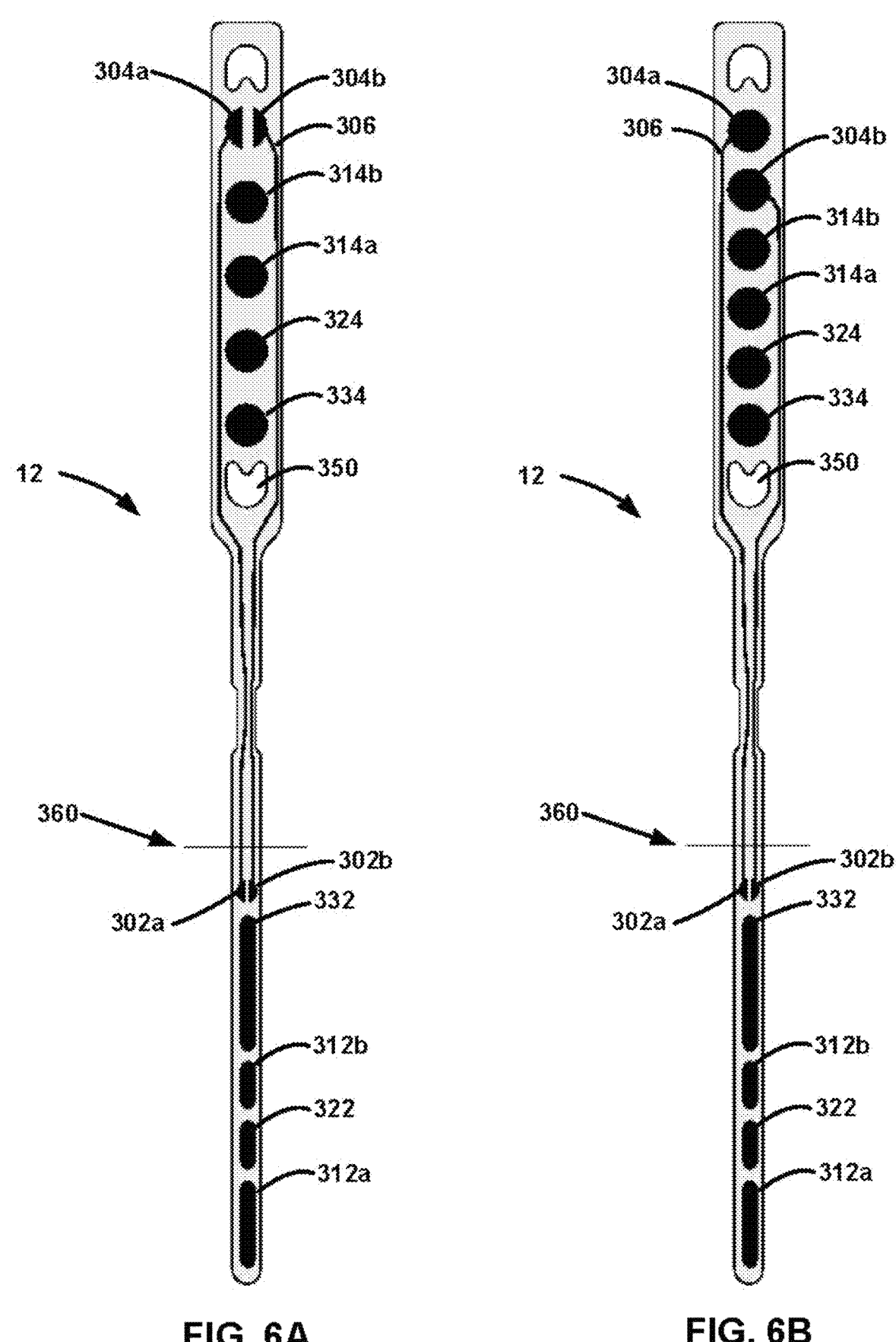
FIG. 6A                  FIG. 6B

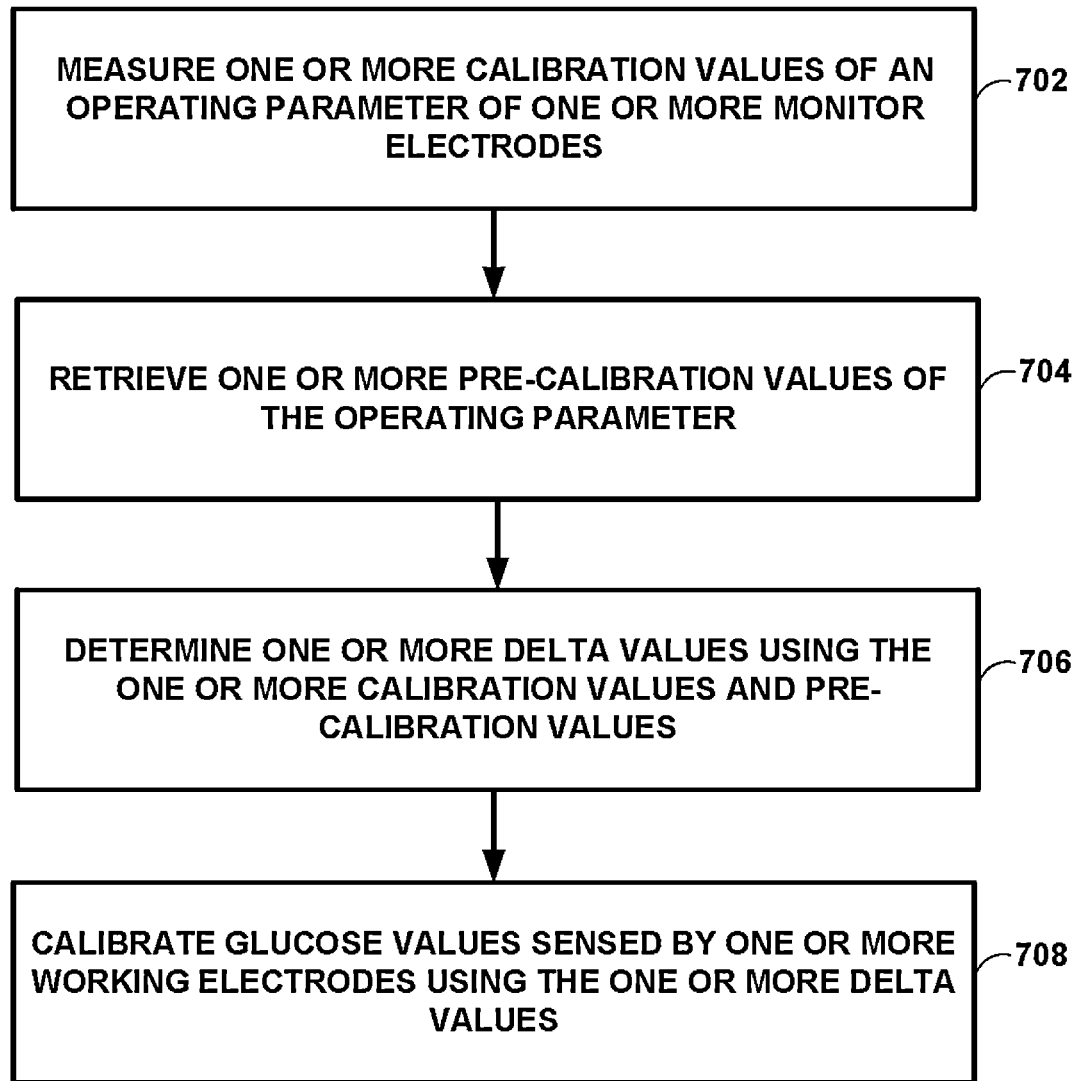

MEASURE ONE OR MORE CALIBRATION VALUES OF AN OPERATING PARAMETER OF ONE OR MORE MONITOR ELECTRODES ⟋702

RETRIEVE ONE OR MORE PRE-CALIBRATION VALUES OF THE OPERATING PARAMETER ⟋704

DETERMINE ONE OR MORE DELTA VALUES USING THE ONE OR MORE CALIBRATION VALUES AND PRE-CALIBRATION VALUES ⟋706

CALIBRATE GLUCOSE VALUES SENSED BY ONE OR MORE WORKING ELECTRODES USING THE ONE OR MORE DELTA VALUES ⟋708

FIG. 7

SENSOR DEVICE MONITORS FOR CALIBRATION

TECHNICAL FIELD

This disclosure generally relates to sensor technology, including sensors used for sensing a variety of physiological parameters.

BACKGROUND

A variety of sensors have been developed for detecting and/or quantifying specific agents or compositions in a patient's body, which enable patients and medical personnel to monitor physiological conditions within the patient's body. Illustratively, subjects may wish to monitor glucose levels in a subject's body via glucose sensors. Glucose sensors are configured to detect and/or quantify the amount of glucose in a patient's body (e.g., interstitial glucose, blood glucose). In some examples, it may be beneficial to monitor glucose levels on a continuing basis (e.g., in a diabetic patient). Thus, glucose sensors have been developed for use in obtaining an indication of glucose levels in a diabetic patient. Such readings are useful in monitoring and/or adjusting a treatment regimen which typically includes the regular administration of insulin to the patient.

A patient can measure their glucose using a glucose measurement device (i.e., glucose meter), such as a test strip meter. A continuous glucose measurement system (or a continuous glucose monitor (CGM)) may be configured to determine glucose levels in a patient. A hospital hemocue may also be used to determine glucose levels. CGMs may be beneficial for patients who desire to take more frequent glucose measurements. Some example CGM systems include subcutaneous (or short-term) sensors and implantable (or long-term) sensors.

SUMMARY

In general, this disclosure describes techniques for calibrating a medical device (e.g., a continuous glucose monitor or "CGM") based on measured changes in the operating parameters of one or more monitor electrodes. Changes in operating parameters of working electrodes of the medical device may be indicative of physiological parameters of a patient, such as changes in glucose level (e.g., interstitial glucose level, blood glucose level). To accurately measure physiological parameters of a patient, the medical device should be calibrated to account for environmental effects on the electrodes of the medical device. In some examples, this disclosure describes techniques and devices for determining environmental effects on the chemistry stack of working electrodes of a CGM between assembly and installation of the CGM, based on the measured changes in the chemistry stack of the monitor electrodes.

Values sensed by the working electrodes of a medical device (e.g., glucose monitor) are typically calibrated after assembly of the medical device. That calibration is relied upon when the medical device is installed on or in a patient and the working electrodes begin measurements of patient parameters. However, the medical device (and subsequently the working electrodes) may have been subject to a variety of environmental conditions between assembly and installation that are unaccounted for by the earlier calibration. In particular, medical devices typically go through a sterilization process, a shipping process, and a storage period in which the medical device may be exposed to different environments that may alter the sensing properties of the working electrodes.

This disclosure describes devices and techniques for positioning one or more monitor electrodes of a medical device near the working electrodes, and determining a change in calibration for values sensed by the working electrodes using a change in operating parameters of the monitor electrodes. The one or more monitor electrodes may have the same chemistry stack as the working electrodes, one or more different chemistry stacks, or a combination thereof. By measuring a difference in an operating parameter (e.g., resistance, capacitance, impedance) of the one or more monitor electrodes both after assembly of the medical device, and before installation, it may be possible to determine any environmental effects on the one or more chemistry stacks of the one or more monitor electrodes. That difference can be translated to a change in the chemistry stack of the working electrodes, and subsequently the operating parameters of the working electrodes in order to calibrate them.

In some examples, a system for monitoring glucose includes processing circuitry and a glucose monitor including one or more monitor electrodes and one or more working electrodes, wherein a first chemistry stack is disposed on at least one monitor electrode of the one or more monitor electrodes and a second chemistry stack is disposed on at least one working electrode of the one or more working electrodes. The processing circuitry may be configured to: measure one or more calibration values of an operating parameter of one or more monitor electrodes; retrieve one or more pre-calibration values of the operating parameter of the one or more monitor electrodes, wherein the one or more pre-calibration values were measured before the calibration value; determine one or more delta values using the one or more calibration values and the one or more pre-calibration values; and calibrate glucose values sensed by the one or more working electrodes using the one or more delta values.

In some examples, a method includes: measuring one or more calibration values of an operating parameter of one or more monitor electrodes, wherein a first chemistry stack is disposed on at least one monitor electrode of the one or more monitor electrodes; retrieving one or more pre-calibration values of the operating parameter of the one or more monitor electrodes, wherein the one or more pre-calibration values were measured before the calibration value; determining one or more delta values using the one or more calibration values and the one or more pre-calibration values; and calibrating glucose values sensed by the one or more working electrodes using the one or more delta values, wherein a second chemistry stack is disposed on at least one working electrode of the one or more working electrodes.

In some examples, a glucose monitor includes: one or more working electrodes; one or more monitor electrodes; a first chemistry stack disposed on at least one monitor electrode of the one or more monitor electrodes, wherein the first chemistry stack has a first reaction to environmental conditions; and a second chemistry stack disposed on at least one working electrode of the one or more working electrodes, wherein the second chemistry stack has a second reaction to the environmental conditions that can be determined based on the first reaction.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIG. 3A is a conceptual drawing illustrating an example sensor flex comprising one or more monitor electrodes in accordance with one or more examples described in this disclosure.

FIG. 3B is a conceptual drawing illustrating another example sensor flex comprising one or more monitor electrodes in accordance with one or more examples described in this disclosure.

FIG. 4A is a conceptual drawing illustrating the front side of an example sensor flex comprising one or more monitor electrode contacts on the back of the sensor flex in accordance with one or more examples described in this disclosure.

FIG. 4B is a conceptual drawing illustrating the back side of an example sensor flex comprising one or more monitor electrode contacts on the back of the sensor flex in accordance with one or more examples described in this disclosure.

FIG. 6A is a conceptual drawing illustrating an example sensor flex comprising one or more subcutaneous monitor electrodes in accordance with one or more examples described in this disclosure.

FIG. 6B is a conceptual drawing illustrating another example sensor flex comprising one or more subcutaneous monitor electrodes in accordance with one or more examples described in this disclosure.

FIG. 7 is a flowchart illustrating an example technique of the disclosure.

DETAILED DESCRIPTION

Figure 1:
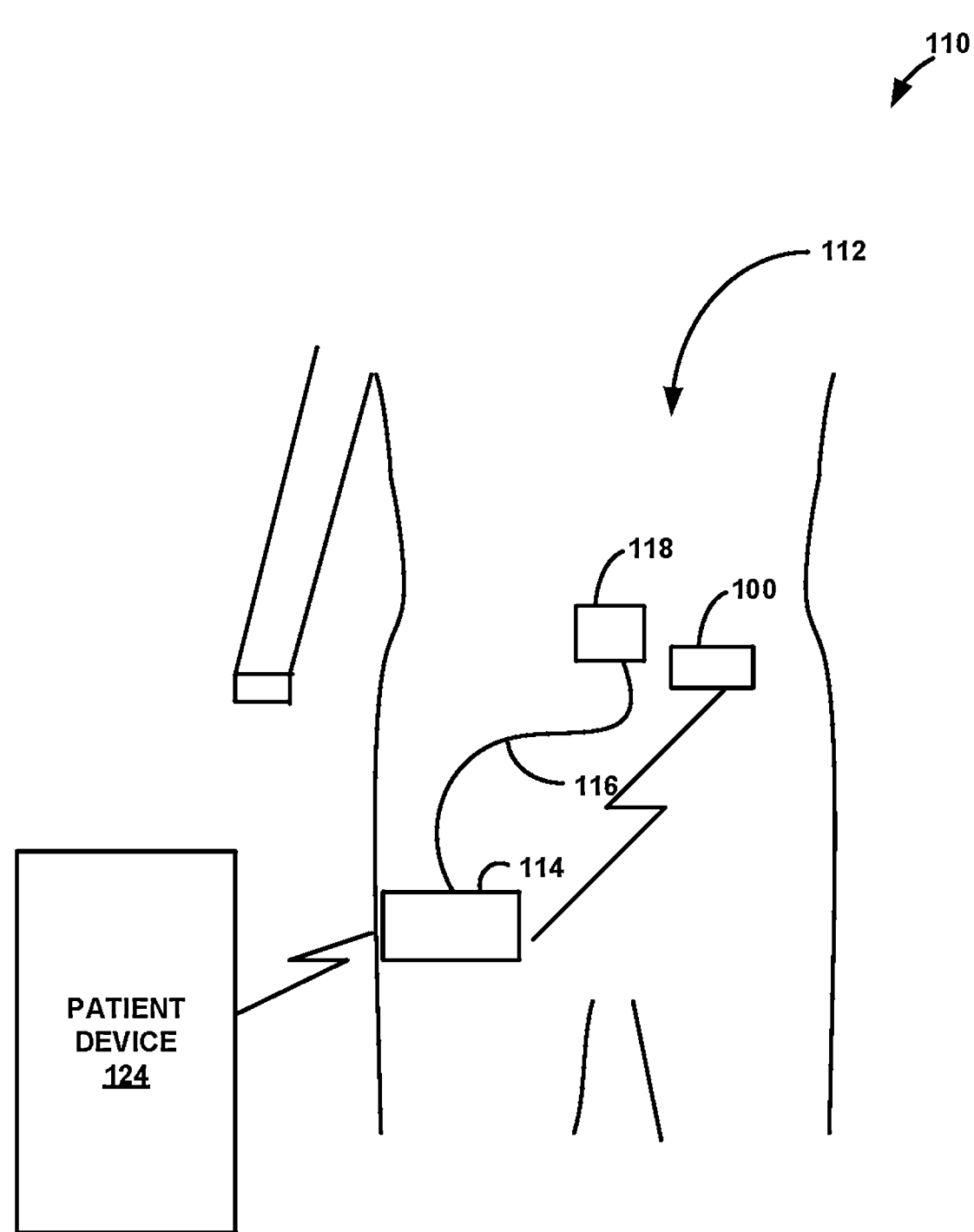
FIG. 1 is a conceptual diagram illustrating an example system that includes an implantable medical device (IMD) configured to measure the glucose of a patient in accordance with one or more examples described in this disclosure.

A system may include a glucose monitor with an electrochemical cell which is used to determine a glucose level of a patient (e.g., interstitial glucose level, blood glucose level). The electrochemical cell may apply electrical energy via one or more electrodes (e.g., monitor electrodes) displaced within a fluid and/or tissue of a patient, and based on a measured operating parameter (e.g., current, impedance, resistance, capacitance) of the one or more electrodes, determine the glucose level (a value indicative of an amount of glucose present at the electrodes). A correlation between the operating parameter and the glucose value may depend on one or more chemistry stacks on the one or more electrodes. Glucose values sensed by the one or more electrodes of the glucose monitor may be calibrated against known glucose values and known measurements of operating parameters after assembly of the glucose monitor to obtain a pre-calibration value.

However, after the glucose monitor is assembled and pre-calibrated, it may undergo sterilization, shipping, and storage procedures where the glucose monitor is subject to different environments for different amounts of time. The different environments and length of time spent in each environment may affect the composition of the one or more chemistry stacks on the one or more electrodes. A changed composition of the chemistry stacks on the one or more electrodes may change the correlation between the operating parameter and the glucose value. This disclosure describes example techniques to calibrate the glucose monitor just before, during, or just after installation into a patient to determine if there is a change in correlation. Moreover, this disclosure describes example techniques to account for any change in the correlation and calibrating values sensed by the glucose monitor due to the change in the correlation so as to generate more accurate glucose values for the patient.

A system may include a glucose monitor with one or more working electrodes and one or more monitor electrodes, where each electrode of the working electrodes and monitor electrodes has a chemistry stack. The one or more monitor electrodes may have the same chemistry stack as the working electrodes, one or more different chemistry stacks, or a combination thereof. The system may also include processing circuitry configured to measure one or more calibration values of an operating parameter of the one or more monitor electrodes just before installation of the glucose monitor on the patient. The one or more calibration values may reflect changes in the chemistry stack of the monitor electrodes since manufacture/assembly of the glucose monitor. By analyzing a difference between a pre-calibration value for the monitor electrodes (e.g., where the pre-calibration value was determined at the time of manufacture/assembly and before any changes to the chemistry stack from shipping, storage, etc.) and the calibration value for the monitor electrodes, the processing circuitry may determine a change in the chemistry stack of the working electrodes. The processing circuitry may update the operating parameters of the working electrodes so that the glucose monitor provides more accurate glucose levels. That is, rather than relying on the operating parameters of the working electrodes from the time of manufacture to determine the glucose values, the processing circuitry may determine the glucose values based on the actual operating parameters of the working electrodes upon use. Again, the actual operating parameters of the working electrodes may have changed after manufacturing due to storage, shipping, etc.

The processing circuitry may be configured to automatically measure the one or more calibration values of the operating parameter of the one or more monitor electrodes. In some examples, removing a cap of a glucose monitor may trigger processing circuitry to take the measurement. In some examples, inserting the glucose monitor into patient tissue may trigger processing circuitry to take the measurement. In some examples processing circuitry may be configured to periodically take the measurement. In some examples, a button or other mechanical trigger on the glucose monitor may trigger processing circuitry to take the measurement. In some examples, processing circuitry may receive a wireless signal from a patient device or other external device that triggers processing circuitry to take the measurement.

FIG. 1 is a conceptual diagram illustrating an example system 110 that includes an implantable medical device (IMD) configured to measure the glucose levels of a patient in accordance with one or more examples described in this disclosure. FIG. 1 illustrates system 110 that includes insulin pump 114, tubing 116, infusion set 118, glucose monitor 100 (e.g., a glucose level monitoring device comprising a glucose sensor), and patient device 124. Insulin pump 114 may be described as a tethered pump, because tubing 116 tethers insulin pump 114 to infusion set 118. In some examples, rather than utilizing a tethered pump system comprising insulin pump 114, tubing 116, infusion set 118, and/or glucose monitor 100, patient 112 may utilize a patch pump. Instead of delivering insulin via tubing and an infusion set, a pump patch may deliver insulin via a cannula extending directly from an insulin pump. In some examples, a glucose sensor may also be integrated into such an insulin pump (e.g., a so-called "all-in-one (AIO) insulin pump").

Patient 112 may be diabetic (e.g., Type 1 diabetic or Type 2 diabetic), and therefore, the glucose level in patient 112 may be controlled with delivery of supplemental insulin. For example, patient 112 may not produce sufficient insulin to control the glucose level or the amount of insulin that patient 112 produces may not be sufficient due to insulin resistance that patient 112 may have developed.

To receive the supplemental insulin, patient 112 may carry insulin pump 114 that couples to tubing 116 for delivery of insulin into patient 112. Infusion set 118 may connect to the skin of patient 112 and include a cannula to deliver insulin into patient 112. Glucose monitor 100 may also be coupled to patient 112 to measure glucose level in patient 112. Insulin pump 114, tubing 116, infusion set 118, and glucose monitor 100 may together form an insulin pump system. One example of the insulin pump system is the MIN-IMED™ 780G insulin pump system by MEDTRONIC MINIMED, INC. However, other examples of insulin pump systems may be used, and the example techniques should not be considered limited to the MINIMED™ 780G insulin pump system. For example, the techniques described in this disclosure may be utilized with any insulin pump and/or glucose monitoring system that includes an in vivo glucose sensor (e.g., a continuous glucose monitor or other in vivo glucose sensor).

Glucose monitor 100 may include a sensor that is inserted under the skin of patient 112 (e.g., in vivo), such as near the stomach of patient 112 or in the arm of patient 112 (e.g., subcutaneous connection). The sensor of glucose monitor 100 may be configured to measure the interstitial glucose level, which is the glucose found in the fluid between the cells of patient 112. Glucose monitor 100 may be configured to continuously or periodically sample the glucose level and rate of change of the glucose level over time.

In one or more examples, insulin pump 114, glucose monitor 100, and/or the various components illustrated in FIG. 1, may together form a closed-loop therapy delivery system. For example, patient 112 may set a target glucose level, usually measured in units of milligrams per deciliter, on insulin pump 114. Insulin pump 114 may receive the current glucose level from glucose monitor 100 and, in response, may increase or decrease the amount of insulin delivered to patient 112. For example, if the current glucose level is higher than the target glucose level, insulin pump 114 may increase the insulin. If the current glucose level is lower than the target glucose level, insulin pump 114 may temporarily cease delivery of the insulin. Insulin pump 114 may be considered as an example of an automated insulin delivery (AID) device. Other examples of AID devices may be possible, and the techniques described in this disclosure may be applicable to other AID devices.

Insulin pump 114 and glucose monitor 100 may be configured to operate together to mimic some of the ways in which a healthy pancreas works. Insulin pump 114 may be configured to deliver basal dosages, which are small amounts of insulin released continuously throughout the day. There may be times when glucose levels increase, such as due to eating or some other activity that patient 112 undertakes. Insulin pump 114 may be configured to deliver bolus dosages on demand in association with food intake or to correct an undesirably high glucose level in the bloodstream. In one or more examples, if the glucose level rises above a target level, then insulin pump 114 may deliver a bolus dosage to address the increase in glucose level. Insulin pump 114 may be configured to compute basal and bolus dosages and deliver the basal and bolus dosages accordingly. For instance, insulin pump 114 may determine the amount of a basal dosage to deliver continuously and then determine the amount of a bolus dosage to deliver to reduce glucose level in response to an increase in glucose level due to eating or some other event.

Accordingly, in some examples, glucose monitor 100 may sample glucose levels for determining rate of change in glucose level over time. Glucose monitor 100 may output the glucose level to insulin pump 114 (e.g., through a wireless link connection like BLUETOOTH). Insulin pump 114 may compare the glucose level to a target glucose level (e.g., as set by patient 112 or a clinician) and adjust the insulin dosage based on the comparison. In some examples, insulin pump 114 may adjust insulin delivery based on a predicted glucose level (e.g., where glucose level is expected to be in the next 30 minutes).

As described above, patient 112 or a clinician may set one or more target glucose levels on insulin pump 114. There may be various ways in which patient 112 or the clinician may set a target glucose level on insulin pump 114. As one example, patient 112 or the clinician may utilize patient device 124 to communicate with insulin pump 114. Examples of patient device 124 include mobile devices, such as smartphones, tablet computers, laptop computers, and the like. In some examples, patient device 124 may be a special programmer or controller (e.g., a dedicated remote-control device) for insulin pump 114. Although FIG. 1 illustrates one patient device 124, in some examples, there may be a plurality of patient devices. For instance, system 110 may include a mobile device and a dedicated wireless controller, each of which is an example of patient device 124. For ease of description only, the example techniques are described with respect to patient device 124 with the understanding that patient device 124 may be one or more patient devices.

Patient device 124 may also be configured to interface with glucose monitor 100. As one example, patient device 124 may receive information from glucose monitor 100 through insulin pump 114, where insulin pump 114 relays the information between patient device 124 and glucose monitor 100. As another example, patient device 124 may receive information (e.g., glucose level or rate of change of glucose level) directly from glucose monitor 100 (e.g., through a wireless link).

In one or more examples, patient device 124 may comprise a user interface with which patient 112 or the clinician may control insulin pump 114. For example, patient device 124 may comprise a touchscreen that allows patient 112 or the clinician to enter a target glucose level. Additionally or alternatively, patient device 124 may comprise a display device that outputs the current and/or past glucose level. In some examples, patient device 124 may output notifications to patient 112, such as notifications if the glucose level is too high or too low, as well as notifications regarding any action that patient 112 needs to take. In some examples, glucose monitor 100 and insulin pump 114 of an insulin pump system may be packaged together such that an electrochemical cell or working electrode of the glucose sensor may be placed relatively near an insulin delivery site on the patient.

Glucose monitor 100 may be configured to determine one or more operating parameters of electrodes of glucose monitor 100. Operating parameters may include, for example, a voltage, an electrical current, or an impedance. In general, the electrical current flowing through a sensing (e.g., working) electrode of glucose monitor 100 is indicative of the glucose level in the patient's interstitial fluid. In some examples, the working electrode may be part of an electrochemical cell configured to measure voltage, interstitial signal (iSig), or impedances.

In accordance with the techniques, device, and systems disclosed herein, a glucose monitor 100 may include one or more working electrodes and one or more monitor electrodes. Glucose monitor 100 may use the working electrodes to sense glucose values in a patient. The monitor electrodes may be manufactured with an identical structure and/or composition to the working electrodes, and processing circuitry of the system that includes glucose monitor 100 may use the monitor electrodes to calibrate the working electrodes just before or during installation of glucose monitor 100.

Each of the one or more working electrodes may be positioned on a sensor flex of glucose monitor 100. In some examples, one or more of the monitor electrodes may be positioned adjacent one or more of the working electrodes on the sensor flex. The proximity of the monitor electrodes to the working electrodes may ensure that both the monitor electrodes and working electrodes are subject to substantially the same environmental conditions from the time glucose monitor 100 is assembled (and the electrodes are pre-calibrated) to the time glucose monitor 100 is installed on a patient (and the electrodes are calibrated again).

Processing circuitry of glucose monitor 100 may sense glucose levels in a patient by measuring an operating parameter of one or more working electrodes of glucose monitor 100 and determining a glucose value from the measured operating parameter. For example, processing circuitry may measure the amount of electrical current flowing through the working electrodes, where different amounts of current are indicative of different glucose values in a patient. The relation between electrical current and glucose values may be represented by a formula in memory of glucose monitor 100. The formula may include one or more factors, including one or more calibration factors. The processing circuitry may be configured to measure the one or more calibration factors. A pre-calibration value may be a calibration factor measured by processing circuitry at the time of manufacture/assembly of glucose monitor 100. Alternatively, or in addition, a calibration value may be a calibration factor measured by processing circuitry at the time of installation of glucose monitor 100 on a patient. When processing circuitry measures a new calibration factor, it may calibrate the glucose values sensed by the one or more working electrodes by replacing an old calibration factor in the formula with the new calibration factor. In this way, processing circuitry may update the calibration of glucose monitor 100 based on the actual environment glucose monitor 100 will be operating in, rather than relying solely on a calibration made at the time of assembly, manufacture, or initial calibration.

Processing circuitry may measure a calibration factor for one or more electrodes by measuring an operating parameter of the one or more electrodes and determining a glucose value from the measured operating parameter using the formula in memory. Processing circuitry may compare the determined glucose value to a known or given glucose value. Processing circuitry may determine what calibration factor is necessary (the measured calibration factor), when implemented in the formula, to arrive at the known or given glucose value.

Processing circuitry of the system which includes glucose monitor 100 may be configured to measure one or more pre-calibration values of an operating parameter of one or more electrodes of glucose monitor 100 at the time of manufacture/assembly of glucose monitor 100. The processing circuitry may then store the pre-calibration values in a memory of the system. Before or during installation of glucose monitor 100, the processing circuitry may measure one or more calibration values of the same operating parameter of one or more monitor electrodes of glucose monitor 100. Processing circuitry may retrieve the one or more pre-calibration values from memory and determine one or more delta values using the one or more pre-calibration values and the one or more calibration values.

For example, processing circuitry may determine a delta value for a first monitor electrode having a first chemistry stack by subtracting the calibration value for the first monitor electrode with the first chemistry stack from the pre-calibration value for the first monitor electrode with the first chemistry stack for a given calibration point. In some examples, the processing circuitry may determine a delta value for each monitor electrode of the one or more monitor electrodes. In some examples, the processing circuitry may determine a single delta value for the monitor electrodes by averaging the delta values for each monitor electrode, or determining a delta value based on an operating parameter of multiple monitor electrodes at once. For example, processing circuitry may measure an operating parameter such as a voltage across multiple monitor electrodes.

The delta values may reflect changes in the chemistry stack of the one or more monitor electrodes due to environmental effects since manufacture/assembly of the glucose monitor. Environmental effects may have also caused changes in the chemistry stacks of the one or more working electrodes that are difficult to measure directly.

Processing circuitry may calibrate glucose values sensed by one or more working electrodes based on the determined one or more delta values. Processing circuitry may translate the one or more delta values to a change in an operating parameter of the one or more working electrodes. Using transfer functions or lookup tables, processing circuitry of glucose sensor 100 may determine a new calibration factor for the one or more working electrodes based on the one or more delta values for calibration values of the monitor electrodes. The new calibration factor for the working electrodes may differ from an old calibration factor for the working electrodes, where the old calibration factor was determined around the time of manufacture/assembly of glucose monitor 100. The change in calibration factor for the one or more working electrodes reflects a change in the measured operating parameter of the one or more working electrodes when exposed to the same glucose levels. In some examples, the one or more monitor electrodes each have a different chemistry stack, and processing circuitry may use a different lookup table or transfer function to determine a new calibration value for the one or more working electrodes. In some examples, the one or more monitor electrodes each have the same chemistry stack. Processing circuitry may take an average of all determined new calibration values for each of the one or more working electrodes. Processing circuitry may use the average new calibration value for a working electrode to calibrate the glucose levels sensed by that working electrode.

Changes in the chemistry stacks of the one or more working electrodes may be difficult to measure directly for a number of reasons. A glucose monitor may not be designed to allow easy measurement of operating parameters of the working electrodes. A glucose monitor may include at least two working electrodes, each with a different chemistry stacks to sense glucose levels more effectively. Because of the differing chemistry stacks, it may be difficult to measure a difference signal between the two working electrodes. It is easier to measure a difference signal across two monitor electrodes having the same chemistry stacks. If two monitor electrodes are located adjacent one another in the glucose monitor, it may be easier during manufacture and assembly to cover them with nearly identical chemistry stacks. If two monitor electrodes are located adjacent one another in the glucose monitor, there may be less chance of errors in a measured difference signal across the monitor electrodes due to outside interference. Furthermore, the chemistry stacks on the one or more monitor electrodes may be designed to react more to aging or environmental effects, aiding in the accuracy of transfer functions to determine the effects of the environment on the chemistry stacks of the working electrodes. For example, a chemistry stack may be designed to oxidize more slowly or quickly when in contact with air. In some examples, a chemistry stack may be designed change its chemistry with exposure to specific gasses. In some examples, a chemistry stack may react to environmental effects by reducing the number of active glucose oxidase molecules on the stack. In some examples, a chemistry stack may absorb moisture from its environment (e.g., a chemistry stack containing a silica gel), including absorbing more moisture when exposed to more environmental moisture.

Glucose monitor 100 may also include a circuit board. At least a portion of the sensor flex may be positioned next to the circuit board to allow contacts between the electric components of the sensor flex and the other circuitry of glucose monitor 100. In some examples, the electrodes of glucose monitor 100 may be positioned on a first side of the sensor flex, and the circuit board may be positioned on a second side of the sensor flex. Contacts for the electrodes may also be positioned on the second side of the sensor flex, so that the electrode contacts may be connected directly to the circuit board. In some examples, the electrodes of glucose monitor 100 may be positioned on the same side of the sensor flex as the circuit board, and the electrode contacts may be positioned on the opposite side of the sensor flex from the circuit board. Elastomeric connectors (e.g., zebra strips) may electrically connect the electrode contacts on one side of the sensor flex to the circuit board on the other side of the sensor flex.

In examples where electrodes are positioned on the same side of the sensor flex as the circuit board, a hole may need to be machined out of the circuit board to expose the electrodes to the ambient environment. In some examples, the circuit board may be pre-formed with an opening in a location corresponding to the location of the electrodes on the sensor flex when the sensor flex is positioned next to the circuit board in glucose monitor 100.

In some examples, the monitor electrodes of glucose monitor 100 may be positioned on the sensor flex such that when glucose monitor 100 is installed on a patient, the monitor electrodes are positioned subcutaneously, along with the working electrodes. In some examples, the monitor electrodes may be configured to operate as backup or supplementary working electrodes, reference electrodes, or counter electrodes after installation. In some examples, glucose monitor 100 may include two monitor electrodes positioned adjacent one another on the sensor flex.

It may be easier to determine operating parameters (e.g., resistance, capacitance, impedance) of the monitor electrodes than the working electrodes, as the working electrodes may not be designed to take measurements of certain operating parameters. For example, the working electrodes may have a chemistry stack designed to most accurately measure a glucose level, while the monitor electrodes may have a chemistry stack designed to change an operating parameter of the monitor electrodes in response to an environmental effect. In some examples, the circuitry for the working electrodes may be configured to most effectively measure a glucose level, whereas the circuitry of the monitor electrodes may be configured to more effectively measure varying operating parameters of the monitor electrodes. In examples where the one or more monitor electrodes are positioned adjacent one another, it may be easier to apply a chemistry stack to the monitor electrodes during manufacture and/or assembly. The chemistry stack may be applied to all adjacent monitor electrodes at once-rather than iteratively-resulting in a faster process, a more consistent chemistry stack between the different monitor electrodes, and an increased consistency of measurements across the monitor electrodes.

A system for monitoring glucose may include a glucose monitor with one or more monitor electrodes and one or more working electrodes. A first chemistry stack may be disposed on at least one of the one or more monitor electrodes, and may have a first reaction to environmental conditions. A second chemistry stack may be disposed on at least one of the one or more working electrodes, and may have a second reaction to the environmental conditions. In some examples, the first chemistry stack may be identical to the second chemistry stack. In other examples the first chemistry stack may include different chemicals, or thicknesses of layers of the chemicals in the first chemistry stack than the second chemistry stack.

The system for monitoring glucose may also include processing circuitry configured to determine the reaction of chemistry stacks to environmental conditions by measuring an operating parameter of the one or more monitor electrodes before and after exposure to environmental conditions. For example, processing circuitry may retrieve one or more pre-calibration values (a calibration factor measured by processing circuitry at the time of manufacture/assembly of glucose monitor 100) of an operating parameter of the one or more monitor electrodes and measure one or more calibration values (a calibration factor measured by processing circuitry at the time of installation of glucose monitor 100 on a patient) of the operating parameter of the one or more monitor electrodes. Processing circuitry may determine one or more delta values as described above using the one or more calibration values and the one or more pre-calibration values. The one or more delta values may represent changes in the chemistry stacks of the one or more monitor electrodes. The changes in the chemistry stacks of the one or more monitor electrodes reflect the reaction of the chemistry stacks to environmental conditions. In this manner, processing circuitry may determine the reaction of chemistry stacks to environmental conditions.

Processing circuitry may determine a reaction of one or more chemistry stacks on one or more working electrodes of glucose monitor 100 by using transfer functions or lookup tables, along with the one or more delta values, to determine new calibration factors for the one or more working electrodes. The new calibration factors for the one or more working electrodes will reflect changes in the chemistry stacks of the working electrodes to environmental conditions experienced by the chemistry stacks on the working electrodes, and hence will also reflect the reaction of the chemistry stacks on the working electrodes to environmental conditions.

In some examples, a system may include glucose monitor 100 with at least two monitor electrodes with different chemistry stacks on each monitor electrodes. For example, a first chemistry stack having a first reaction to environmental conditions may be disposed on a first monitor electrode, a second chemistry stack having a second reaction to environmental conditions may be disposed on a second monitor electrode, and a third chemistry stack having a third reaction to environmental conditions may be disposed on one or more working electrodes of glucose monitor 100. Processing circuitry may determine the third reaction based on one or more of the first reaction and the second reaction, using lookup tables and/or transfer functions. Although processing circuitry may determine the third reaction based on either of the first reaction or second reaction, the accuracy of the third reaction may be increased by determining the third reaction based on a combination of both the first reaction and the second reaction.

In examples where the system includes both a first monitor electrode having a first chemistry stack and a second monitor electrode having a second chemistry stack, processing circuitry of the system may be configured to measure one or more calibration values of an operating parameter of each monitor electrode. For example, processing circuitry may retrieve a first pre-calibration value of the operating parameter of the first monitor electrode having the first chemistry stack and retrieve a second pre-calibration value of the operating parameter of the second monitor electrode having the second chemistry stack. The pre-calibration values may be stored in memory of glucose monitor 100 as described above, and measured around the time of manufacture/assembly of glucose monitor 100. Processing circuitry may also measure a first calibration value of the operating parameter of the first monitor electrode and measure a second calibration value of the operating parameter of the second monitor electrode. The operating parameter used to measure calibration values may be the same or differ between monitor electrodes, so long as the pre-calibration value retrieved by processing circuitry is based on the same operating parameter. Processing circuitry may determine a first delta value using the first calibration value and the first pre-calibration value and determine a second delta value using the second calibration value and the second pre-calibration value.

Processing circuitry may use the first and second delta values to calibrate the glucose values sensed by the one or more working electrodes of glucose monitor 100. Processing circuitry may use a different lookup table or transfer function for each delta value, where the transfer function or lookup table is specific to the structure of the chemistry stack of the monitor electrode, the structure of the chemistry stack of the working electrode, and the operating parameter measured. Using the transfer functions or lookup tables, processing circuitry may correlate the one or more delta values to one or more new calibration values for the one or more working electrodes. Processing circuitry may take an average of all determined new calibration values for each of the one or more working electrodes. Processing circuitry may use the average new calibration value for a working electrode to calibrate the glucose levels sensed by that working electrode.

In some examples when the at least two monitor electrodes have different chemistry stacks, the first chemistry stack may react more to moisture than the second chemistry stack, and/or the second chemistry stack may react more to temperature than the first chemistry stack. In these examples, the first chemistry stack may have an increased reaction to moisture such that the chemistry stack changes more in response to moisture than other environmental factors. The increased reaction in the chemistry stack may result in a large change in an operating parameter of the monitor electrode with the first chemistry stack before being exposed to moisture and after being exposed to moisture. Similarly, the second chemistry stack may experience a large change in response to different temperature conditions and a relatively small or no change to different moisture conditions. Processing circuitry may use transfer functions or lookup tables to determine the reaction to environmental conditions of a third chemistry stack on one or more working electrodes, based on the first and second chemistry stacks. The chemistry stacks may be manufactured such that they react more to any of a number of environmental conditions (e.g., exposure to light, exposure to nitrogen or other gas, exposure to specific particulate matter, etc.).

In some examples, glucose monitor 100 may include at least two working electrodes with different chemistry stacks on each working electrode. For example, a first chemistry stack having a first reaction to environmental conditions may be disposed on a first working electrode, a second chemistry stack having a second reaction to environmental conditions may be disposed on a second working electrode, and a third chemistry stack having a third reaction to environmental conditions may be disposed on one or more monitor electrodes of glucose monitor 100. Processing circuitry may determine the first reaction and second reaction based on the third reaction, using lookup tables and/or transfer functions for the relationship between the third reaction and each of the first reaction and second reaction. Processing circuitry may determine one or more delta values for one or more operating parameters of the one or more monitor electrodes as described above, and calibrate glucose values sensed by the first working electrode and the second working electrode using the same one or more delta values. Processing circuitry may use a different transfer function or lookup table for each combination of monitor electrode chemistry stack, operating parameter, and working electrode chemistry stack.

The chemistry stacks on each of the electrodes may include one or more of a glucose oxidase (GOx) enzyme layer, a glucose limiting membrane (GLM), a high-density amine, silica gel, a polymer sensitive to environmental changes, or other substance in varying thicknesses and/or concentrations.

Figure 2:
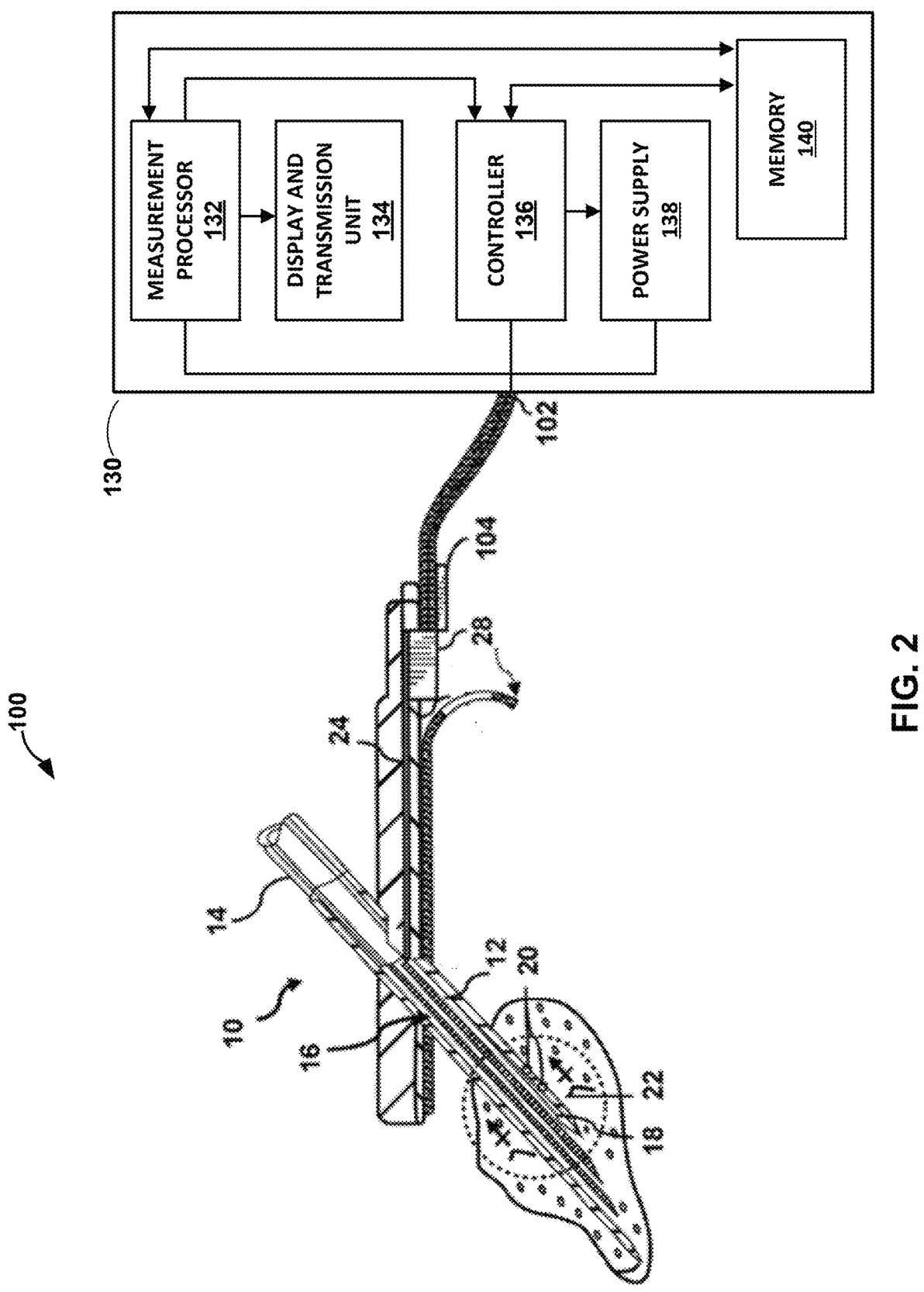
FIG. 2 is a block diagram illustrating an example glucose sensor in accordance with one or more examples described in this disclosure.

FIG. 2 is a block diagram illustrating an example glucose sensor, such as glucose monitor 100, in accordance with one or more examples described in this disclosure.

As illustrated in FIG. 2, subcutaneous sensor set 10 is provided for subcutaneous placement of an active portion of a flexible glucose sensor—sensor flex 12—at a selected site in the body of patient 112. The subcutaneous or percutaneous portion of sensor set 10 includes a hollow, slotted insertion needle 14, and cannula 16. Needle 14 is used to facilitate quick and easy subcutaneous placement of cannula 16 at the subcutaneous insertion site. Inside cannula 16 is glucose sensing portion 18 of glucose sensor 12, which is configured to expose one or more glucose sensor electrodes 20 to the bodily fluids (e.g., blood or interstitial fluid) of patient 112 through window 22 formed in cannula 16. In one example, one or more glucose sensor electrodes 20 may include one or more working electrodes, one or more counter electrodes, one or more reference electrodes, and one or more monitor electrodes. Examples different electrodes are described in more detail with respect to FIGS. 3A-6B. After insertion, insertion needle 14 is withdrawn to leave cannula 16 with glucose sensing portion 18 and glucose sensor electrodes 20 in place at the selected insertion site.

In some examples, subcutaneous sensor set 10 facilitates accurate placement of flexible thin film electrochemical glucose sensor 12 of the type used for monitoring specific blood parameters representative of a condition of patient 112. Glucose sensor 12 monitors glucose levels in the body, and may be used in conjunction with automated or semi-automated medication infusion pumps of the external or implantable type as described above to control delivery of insulin to patient 112.

Examples of flexible electrochemical glucose sensor 12 are constructed in accordance with thin film mask techniques to include elongated thin film conductors embedded or encased between layers of a selected insulative material such as polyimide film or sheet, and membranes. Glucose sensor electrodes 20 at a tip end of glucose sensing portion 18 are exposed through one of the insulative layers for direct contact with patient blood or other body fluids, when glucose sensing portion 18 (or active portion) of glucose sensor 12 is subcutaneously placed at an insertion site. In some examples, one or more of the monitor electrodes of glucose monitor 100 may be positioned above the skin of patient 112 after insertion. Glucose sensing portion 18 is joined to connection portion 24 that terminates in conductive contact pads, or the like, which are also exposed through one of the insulative layers. In other examples, other types of implantable sensors, such as chemical based, optical based, or the like, may be used.

Connection portion 24 and the contact pads are generally adapted for a direct wired electrical connection to a suitable monitor or sensor electronics device 130 for monitoring a condition of patient 112 in response to signals derived from glucose sensor electrodes 20. Connection portion 24 may be conveniently connected electrically to the monitor or sensor electronics device 130 or by connector block 28. Thus, in accordance with examples of the disclosure, subcutaneous sensor sets 10 may be configured or formed to work with either a wired or a wireless characteristic monitor system.

Glucose sensor electrodes 20 may be used in a variety of sensing applications and may be configured in a variety of ways. For example, glucose sensor electrodes 20 may be used in physiological parameter sensing applications in which some type of biomolecule is used as a catalytic agent. For example, glucose sensor electrodes 20 may be used in a glucose and oxygen sensor having a GOx enzyme catalyzing a reaction with glucose sensor electrodes 20. Glucose sensor electrodes 20, along with a biomolecule or some other catalytic agent, may be placed in a human body in a vascular or non-vascular environment. For example, glucose sensor electrodes 20 and biomolecules may be placed in a vein and be subjected to a blood stream, or may be placed in a subcutaneous or peritoneal region of the human body.

Sensor electronics device 130 may include measurement processor 132, display and transmission unit 134, controller 136, power supply 138, and memory 140. Sensor electronics device 130 may be coupled to the sensor set 10 by cable 102 through a connector that is electrically coupled to connector block 28 of connection portion 24. In other examples, the cable may be omitted and sensor electronics device 130 may include an appropriate connector for direct connection to connection portion 104 of sensor set 10. Sensor set 10 may be modified to have connector portion 104 positioned at a different location, e.g., on top of the sensor set to facilitate placement of sensor electronics device 130 over the sensor set.

In examples of the disclosure, measurement processor 132, display and transmission unit 134, and controller 136 may be formed as separate semiconductor chips. However, other examples may combine measurement processor 132, display and transmission unit 134, and controller 136 into a single or multiple customized semiconductor chips. In general, measurement processor 132 may be configured to receive a current, voltage, and/or impedance from glucose sensor electrodes 20. Glucose sensor electrodes 20 may generate a sensor signal indicative of a concentration of a physiological characteristic being measured. For example, the sensor signal may be indicative of a glucose reading. The sensor signal may be measured at a working electrode of glucose sensor electrodes 20. In an example of the disclosure, the sensor signal may be a current (e.g., iSig) measured at the working electrode. In another example of the disclosure, the sensor signal may be a voltage (e.g., Vcounter) measured at the working electrode of glucose sensor electrodes 20.

Electrical parameters of glucose monitor 100 may include impedance parameters. An example of an impedance parameter may include electrochemical impedance spectroscopy (EIS). EIS may provide additional information in the form of sensor impedance and impedance-related parameters at a plurality of different frequencies. EIS may be used as a technique to measure the electrical impedance of the glucose sensor system as a function of frequency of the current and/or voltage. Electrical impedance as a function of frequency measured via EIS may be used, in conjunction with a properly chosen electrical circuit system model, to infer (e.g., determine and/or calculate) dielectric properties of the glucose sensor as well as certain electrical circuit properties of the model.

Measurement processor 132 receives the sensor signal (e.g., a measured current, voltage, and/or impedance) after the sensor signal is measured at glucose sensor electrodes 20 (e.g., a working electrode). Measurement processor 132 may receive the sensor signal and calibrate the sensor signal utilizing reference values. For example, measurement processor 132 may calibrate the sensor signal utilizing reference values based on a known analyte quantity, e.g., a zero glucose measurement to determine a baseline sensor signal. In some examples, changes to the sensor over time may change the responsivity of the glucose sensor, changing the sensor signal and glucose measurement accuracy. Measurement processor 132 may utilize the reference values to adjust for changes over time. In some examples, glucose monitor 100 may update and or adjust the reference values, e.g., using EIS data or other data. In an example of the disclosure, the reference values are stored in a reference memory (e.g., memory 140) and provided to measurement processor 132. Based on the sensor signals and the reference values, measurement processor 132 may determine a glucose measurement. Measurement processor 132 store the glucose measurements in memory 140. The sensor measurements may be sent to display and transmission unit 134 to be either displayed on a display in a housing of glucose monitor 100 or transmitted to an external device.

Memory 140 may be any type of memory device and may be configured to store glucose measurements produced by measurement processor 132, reference values used to determine glucose measurements from sensor signals, or other data used and/or produced by measurement processor 132 and/or controller 136, including a pre-calibration value reflecting the calibration of glucose monitor 100 after assembly. In some examples, memory 140 may further store software and/or firmware that is executable by measurement processor 132 and/or controller 136.

Sensor electronics device 130 may be a monitor which includes a display-to-display physiological characteristics readings. In some examples, sensor electronics device 130 may be remote from sensor set 10 and communicatively connected to sensor set 10, e.g., via a wired or wireless connection. For example, sensor electronics device 130 may also be installed in a desktop computer, a pager, a television including communications capabilities, a laptop computer, a server, a network computer, a personal digital assistant (PDA), a portable telephone including computer functions, an infusion pump including a display, a glucose sensor including a display, and/or a combination infusion pump/ glucose sensor. Sensor electronics device 130 may be housed in a mobile phone, a network device, a home network device, or an appliance connected to a home network.

Power supply 138 may be a battery. The battery can include three series silver oxide 357 battery cells. In other examples, different battery chemistries may be utilized, such as lithium-based chemistries, alkaline batteries, nickel metalhydride, or the like, and a different number of batteries may be used. Sensor electronics device 130 provides power to the sensor set 10 via power supply 138 through cable 102 and cable connector 104.

Controller 136 may be a processor, digital signal processors (DSPs), application specific integrated circuits (ASICs), field programmable gate arrays (FPGAs), or any other equivalent integrated or discrete logic circuitry. In some examples controller 136 may be configured to cause a specific voltage or current to be output to glucose sensor electrodes 20. Glucose sensor electrodes 20 may receive the voltage level or value. In an example of the disclosure, a counter electrode of glucose sensor electrodes 20 may receive the reference voltage from power supply 138. The application of the voltage level causes glucose sensor electrodes 20 to create a sensor signal (e.g., a current through a working electrode) indicative of a concentration of a physiological characteristic being measured (e.g., blood glucose).

FIGS. 3A and 3B are conceptual drawings illustrating an example sensor flex 12 comprising one or more monitor electrodes 302a and 302b in accordance with one or more examples described in this disclosure. As shown in FIGS. 3A and 3B, sensor flex 12 includes working electrodes 312a and 312b, working electrode contacts 314a and 314b, reference electrode 322, reference electrode contact 324, counter electrode 332, counter electrode contact 334, monitor electrodes 302a and 302b, monitor electrode contacts 304a and 304b, monitor electrode wire 306, connection points 350, and skin level line 360. The contacts on sensor flex 12 may serve as connection points to a circuit board of glucose monitor 100, integrating the electrodes of sensor flex 12 with the rest of the circuitry of glucose monitor 100.

Working electrodes 312a and 312b, reference electrode 322, and counter electrode 332 are positioned on sensor flex 12 below the skin level line 360. Skin level line 360 is a hypothetical line marking the location of the surface of patient 112's skin. The portion of sensor flex 12 below skin level line 360 in FIGS. 3A-6B is positioned inside patient 112 when sensor flex 12 is installed in patient 112. The portion of sensor flex 12 above skin level line 360 in FIGS. 3A-6B is positioned outside patient 112 when sensor flex 12 is installed in patient 112.

At least a portion of sensor flex 12 above skin level line 360 may be positioned within a body of glucose monitor 100. Sensor flex 12 may be connected to glucose monitor at least in part by connection points 350. Anchor members of glucose monitor 100 may pass through connection points 350 to hold sensor flex 12 in place with respect to glucose monitor 100.

As shown in FIG. 3A, monitor electrodes 302a and 302b are positioned adjacent one another latitudinally and monitor electrode contacts 304a and 304b are positioned adjacent one another latitudinally. This arrangement may save room on sensor flex 12, and allow for easy deposition of chemistry stacks on monitor electrodes 302a and 302b during manufacture and assembly. Monitor electrode wire 306 connects monitor electrodes 302a and 302b to monitor electrode contacts 304a and 304b. Wires for other electrodes connecting the other electrodes to their respective contacts are not shown, but may be present on either side of sensor flex 12. Monitor electrodes 302a and 302b may be manufactured to have an identical structure and composition as working electrodes 312a and 312b so that changes in the operating parameters of monitor electrodes 302a and 302b due to environmental conditions are correlated with changes in the operating parameters of working electrodes 312a and 312b due to the same environmental conditions.

As shown in FIG. 3B, monitor electrodes 302a and 302b are positioned adjacent one another latitudinally, and monitor electrode contacts 304a and 304b are positioned adjacent one another longitudinally. The longitudinal arrangement of monitor electrode contacts 304a and 304b may allow monitor electrode contacts 304a and 304b to be larger, making it easier to connect monitor electrode contacts 304a and 304b to a circuit board of glucose monitor 100, and providing a more secure connection between monitor electrode contacts 304a and 304b and the circuit board.

Monitor electrodes 302a and 302b may be positioned above skin level line 360 but below a portion of sensor flex 12 positioned in a body of glucose monitor 100. Monitor electrodes may be positioned inside needle 14, and cannula 16 of glucose monitor 100. As working electrodes 312a and 312b are also located inside needle 14 and cannula 16, monitor electrodes 302a and 302b may be exposed to substantially the same environmental conditions as working electrodes 312a and 312b between assembly and installation of glucose monitor 100.

Each of the electrodes on sensor flex 12 may have a chemistry stack deposited thereon. In some examples, the chemistry stack is the same for multiple electrodes. In some examples, the chemistry stack may be different for any number of different electrodes. For example: working electrode 312a may have a first chemistry stack with a first reaction to environmental conditions; working electrode 312b may have a second chemistry stack with a second reaction to environmental conditions; monitor electrodes 302a and 302b may have a third chemistry stack with a third reaction to environmental conditions; each chemistry stack may be different from one another; and changes to the third chemistry stack may be correlated to changes in the first and second chemistry stacks.

Because changes in the chemistry stack of an electrode may change measured operating parameters of the electrode, by measuring an operating parameter of monitor electrodes 302*a* and 302*b* and determining any changes from a previous measurement of the operating parameter of monitor electrodes 302*a* and 302*b*, processing circuitry may determine a corresponding change in the operating parameter of working electrodes 312*a* and 312*b* using lookup tables and/or transfer functions.

Although FIGS. 3A-6B only show two monitor electrodes, in some examples, sensor flex 12 may have any number of monitor electrodes, where each monitor electrode of the number of monitor electrodes has the same or different chemistry stack from other monitor electrodes. Although FIGS. 3A-4B and 6A-6B only show monitor electrodes 302*a* and 302*b* as half-circle electrodes, in some examples monitor electrodes 302*a* and 302*b* may be larger and slightly more distant from one another, making it easier for different chemistry stacks to be applied to each of monitor electrodes 302*a* and 302*b*.

FIGS. 4A and 4B are conceptual drawings illustrating the front and back side, respectively, of an example sensor flex 12 comprising one or more monitor electrode contacts 304*a* and 304*b* on the back of sensor flex 12 in accordance with one or more examples described in this disclosure. As shown in FIGS. 4A and 4B, sensor flex 12 includes working electrodes 312*a* and 312*b*, working electrode contacts 314*a* and 314*b*, reference electrode 322, reference electrode contact 324, counter electrode 332, counter electrode contact 334, monitor electrodes 302*a* and 302*b*, monitor electrode contacts 304*a* and 304*b*, connection points 350, and skin level line 360. The contacts on sensor flex 12 may serve as connection points to a circuit board of glucose monitor 100, integrating the electrodes of sensor flex 12 with the rest of the circuitry of glucose monitor 100.

Working electrodes 312*a* and 312*b*, reference electrode 322, and counter electrode 332 are positioned on sensor flex 12 below the skin level line 360. Skin level line 360 is a hypothetical line marking the location of the surface of patient 112's skin. The portion of sensor flex 12 below skin level line 360 in FIGS. 3A-6B is positioned inside patient 112 when sensor flex 12 is installed in patient 112. The portion of sensor flex 12 above skin level line 360 in FIGS. 3A-6B is positioned outside patient 112 when sensor flex 12 is installed in patient 112.

At least a portion of sensor flex 12 above skin level line 360 may be positioned within a body of glucose monitor 100. Sensor flex 12 may be connected to glucose monitor at least in part by connection points 350. Anchor members of glucose monitor 100 may pass through connection points 350 to hold sensor flex 12 in place with respect to glucose monitor 100.

As shown in FIGS. 4A and 4B, monitor electrodes 302*a* and 302*b* are positioned adjacent one another longitudinally on an upper portion of sensor flex 12, and monitor electrode contacts 304*a* and 304*b* are positioned adjacent one another longitudinally on the opposite side of sensor flex 12 directly opposite monitor electrodes 302*a* and 302*b*. The upper portion of sensor flex 12 may be positioned inside the body of glucose monitor 100. This arrangement may save room on sensor flex 12, and allow for easy deposition of chemistry stacks on monitor electrodes 302*a* and 302*b* during manufacture and assembly. Monitor electrodes 302*a* and 302*b* may be connected to monitor electrode contacts 304*a* and 304*b* through sensor flex 12. Connections between other electrodes and their respective contacts are not shown, but many different arrangements are possible and contemplated. The positioning of monitor electrodes 30*a* and 302*b2* in FIG. 4A on an upper portion of sensor flex 12 may allow monitor electrodes 302 in FIG. 4A to be larger than monitor electrodes 302*a* and 302*b* of FIGS. 3A-3B.

Figure 5A:
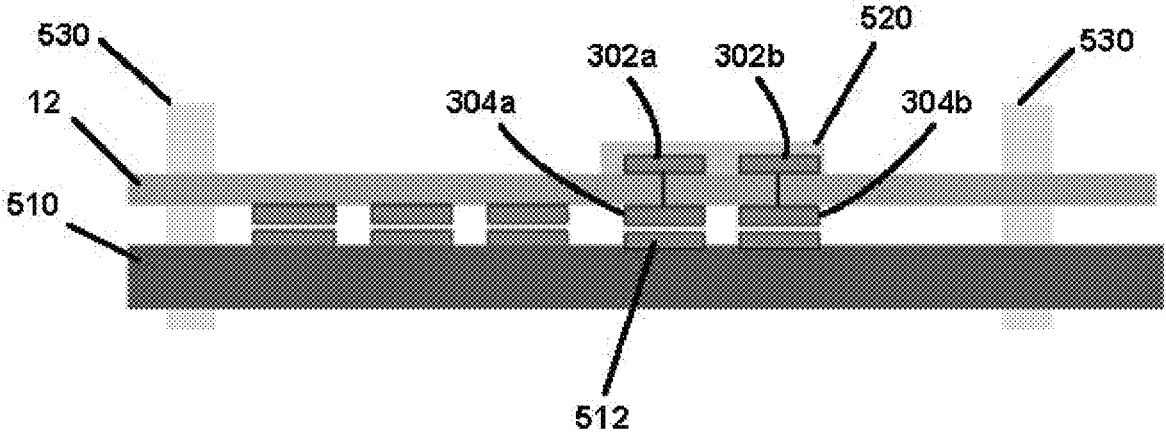
FIG. 5A is a conceptual drawing illustrating an example sensor flex attached to an example circuit board of a medical device in accordance with one or more examples described in this disclosure.
Figure 5B:
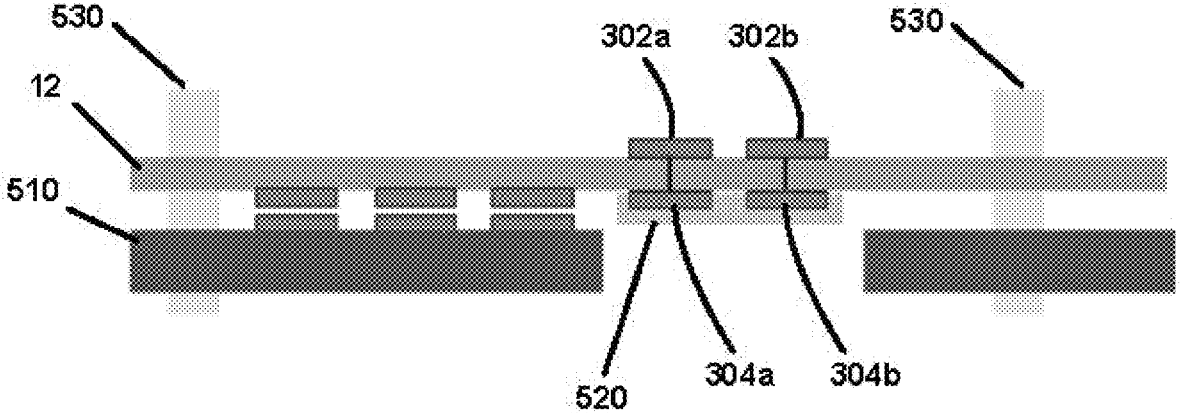
FIG. 5B is a conceptual drawing illustrating another example sensor flex attached to another example circuit board of a medical device in accordance with one or more examples described in this disclosure.

As shown in FIG. 4A, monitor electrodes 302*a* and 302*b* are positioned on the same side of the sensor flex as the contacts for other electrodes, and thus may be positioned on the same side of the sensor flex as the circuit board, as shown in greater detail in FIGS. 5A-5B. The circuit board may have a hole manufactured or machined out in the position where monitor electrodes 302*a* and 302*b* might otherwise contact the circuit board. Monitor electrode contacts 304*a* and 304*b* may be positioned on an opposite side of sensor flex 12 from the circuit board. An elastomeric connector (e.g., zebra strip) may electrically connect monitor electrode contacts 304*a* and 304*b* to the circuit board on the other side of sensor flex 12. Although monitor electrodes 302*a* and 302*b* are depicted as positioned on the same side of sensor flex 12 as the contacts for other electrodes, in some examples, the position of monitor electrodes 302*a* and 302*b* and monitor electrode contacts 304*a* and 304*b* is switched, such that monitor electrode contacts 304*a* and 304*b* are on the same side of the sensor flex as working electrode contacts 314*a* and 314*b*, reference electrode contact 324, counter electrode contact 334, and the circuit board.

Each of the electrodes on sensor flex 12 may have a chemistry stack deposited thereon. In some examples, the chemistry stack is the same for multiple electrodes. Any combination of the same or different chemistry stacks on different electrodes is contemplated. In some examples, the chemistry stack may be different for any number of different electrodes. For example: working electrode 312*a* may have a first chemistry stack with a first reaction to environmental conditions; working electrode 312*b* may have a second chemistry stack with a second reaction to environmental conditions; monitor electrode 302*a* may have a third chemistry stack with a third reaction to environmental conditions; monitor electrode 302*b* may have a fourth chemistry stack with a fourth reaction to environmental conditions; each chemistry stack may be different from one another; changes to the third chemistry stack may be correlated to changes in the first and second chemistry stacks; and changes to the fourth chemistry stack may be correlated to changes in the first and second chemistry stacks.

Because changes in the chemistry stack of an electrode may change measured operating parameters of the electrode, by measuring an operating parameter of monitor electrodes 302*a* and 302*b* and determining any changes from a previous measurement of the operating parameter of monitor electrodes 302*a* and 302*b*, processing circuitry may determine a corresponding change in the operating parameter of working electrodes 312*a* and 312*b* using lookup tables and/or transfer functions.

FIG. 5A is a conceptual drawing illustrating an example sensor flex 12 attached to an example circuit board 510 of a medical device in accordance with one or more examples described in this disclosure.

As shown in FIG. 5A, sensor flex 12 includes monitor electrodes 302*a* and 302*b*, monitor electrode contacts 304*a* and 304*b*, and chemistry stack 520. Sensor flex 12 may be connected to circuit board 510 and glucose monitor 100 by anchor members 530. Monitor electrode contacts 304*a* and 304*b* may be connected to circuit board 510 by circuit board contacts 512. Other electrode contacts and circuit board contacts are pictured, but not labeled.

In the example of FIG. 5A, monitor electrodes 302*a* and 302*b* are located on an opposite side of sensor flex 12 than circuit board 510. Monitor electrode contacts 304*a* and 304*b* are positioned on the same side of sensor flex 12 as circuit board 510, allowing for simple connection between monitor electrode contacts 304a and 304b and circuit board contacts 512. Monitor electrodes 302a and 302b may be positioned on an upper portion of sensor flex 12 inside a body of glucose monitor 100. Monitor electrodes 302a and 302b may be connected to monitor electrode contacts 304a and 304b through sensor flex 12.

FIG. 5B is a conceptual drawing illustrating another example sensor flex 12 attached to another example circuit board 510 of a medical device in accordance with one or more examples described in this disclosure. Sensor flex 12 may be connected to circuit board 510 and glucose monitor 100 by anchor members 530. In the example of FIG. 5B, monitor electrodes 302a and 302b are located on the same side of sensor flex 12 as circuit board 510. In order to expose monitor electrodes 302a and 302b to the environment, a portion of circuit board 510 is machined away, or initially designed out. In some examples, this arrangement is more advantageous than the arrangement of FIG. 5A, as chemistry stack 520 in FIG. 5A may stick out too far from sensor flex 12 and impede a connector block stretching between anchor members 530 that presses sensor flex 12 against circuit board 510. Monitor electrode contacts 304a and 304b are positioned on the opposite side of sensor flex 12 as circuit board 510. Monitor electrode contacts may be connected to contacts of circuit board 510 by an elastomeric connector, wire, or other method. Monitor electrodes 302a and 302b may be positioned on an upper portion of sensor flex 12 inside a body of glucose monitor 100. Monitor electrodes 302a and 302b may be connected to monitor electrode contacts 304a and 304b through sensor flex 12.

FIGS. 6A and 6B are conceptual drawings illustrating example sensor flexes 12 comprising one or more subcutaneous monitor electrodes 302a and 302b in accordance with one or more examples described in this disclosure. As shown in FIGS. 6A and 6B, sensor flex 12 includes working electrodes 312a and 312b, working electrode contacts 314a and 314b, reference electrode 322, reference electrode contact 324, counter electrode 332, counter electrode contact 334, monitor electrodes 302a and 302b, monitor electrode contacts 304a and 304b, monitor electrode wire 306, connection points 350, and skin level line 360. The contacts on sensor flex 12 may serve as connection points to a circuit board of glucose monitor 100, integrating the electrodes of sensor flex 12 with the rest of the circuitry of glucose monitor 100. The electrode contacts may be connected to contacts on the circuit board directly, by means of wires or elastomeric connectors, or another method.

Working electrodes 312a and 312b, monitor electrodes 302a and 302b, reference electrode 322, and counter electrode 332 are positioned on sensor flex 12 below the skin level line 360. Skin level line 360 is a hypothetical line marking the location of the surface of patient 112's skin. The portion of sensor flex 12 below skin level line 360 in FIGS. 3A-6B is positioned inside patient 112 when sensor flex 12 is installed in patient 112. The portion of sensor flex 12 above skin level line 360 in FIGS. 3A-6B is positioned outside patient 112 when sensor flex 12 is installed in patient 112.

At least a portion of sensor flex 12 above skin level line 360 may be positioned within a body of glucose monitor 100. Sensor flex 12 may be connected to glucose monitor at least in part by connection points 350. Anchor members of glucose monitor 100 may pass through connection points 350 to hold sensor flex 12 in place with respect to glucose monitor 100.

As shown in FIG. 6A, monitor electrodes 302a and 302b are positioned adjacent one another latitudinally and monitor electrode contacts 304a and 304b are positioned adjacent one another latitudinally. This arrangement may save room on sensor flex 12, and allow for easy deposition of chemistry stacks on monitor electrodes 302a and 302b during manufacture and assembly. Monitor electrode wire 306 connects monitor electrodes 302a and 302b to monitor electrode contacts 304a and 304b. Wires for other electrodes connecting the other electrodes to their respective contacts are not shown, but may be present on either side of sensor flex 12. Monitor electrodes 302a and 302b may be manufactured to have an identical structure and composition as working electrodes 312a and 312b so that changes in the operating parameters of monitor electrodes 302a and 302b due to environmental conditions are correlated with changes in the operating parameters of working electrodes 312a and 312b due to the same environmental conditions.

As shown in FIG. 6B, monitor electrodes 302a and 302b are positioned adjacent one another latitudinally, and monitor electrode contacts 304a and 304b are positioned adjacent one another longitudinally. The longitudinal arrangement of monitor electrode contacts 304a and 304b may allow monitor electrode contacts 304a and 304b to be larger, making it easier to connect monitor electrode contacts 304a and 304b to a circuit board of glucose monitor 100, and providing a more secure connection between monitor electrode contacts 304a and 304b and the circuit board.

Monitor electrodes 302a and 302b may be positioned below skin level line 360 inside needle 14, and cannula 16 of glucose monitor 100. As working electrodes 312a and 312b are also located below skin level line 360 inside needle 14 and cannula 16, monitor electrodes 302a and 302b may be exposed to substantially the same environmental conditions as working electrodes 312a and 312b during the lifespan of glucose monitor 100.

Each of the electrodes on sensor flex 12 may have a chemistry stack deposited thereon. In some examples, the chemistry stack is the same for multiple electrodes, including monitor electrodes 302a and 302b and one or more working electrodes 312a and 312b. In some examples, the chemistry stack may be different for any number of different electrodes. For example: working electrode 312a may have a first chemistry stack with a first reaction to environmental conditions; working electrode 312b may have a second chemistry stack with a second reaction to environmental conditions; monitor electrodes 302a and 302b may have a third chemistry stack with a third reaction to environmental conditions; each chemistry stack may be different from one another; and changes to the third chemistry stack may be correlated to changes in the first and second chemistry stacks. Any number of different or the same chemistry stacks on different electrodes is contemplated.

Because changes in the chemistry stack of an electrode may change measured operating parameters of the electrode, by measuring an operating parameter of monitor electrodes 302a and 302b and determining any changes from a previous measurement of the operating parameter of monitor electrodes 302a and 302b, processing circuitry may determine a corresponding change in the operating parameter of working electrodes 312a and 312b using lookup tables and/or transfer functions. Processing circuitry may generate an in vivo transfer function or prediction model to account for changes in the operating parameter values based on in vivo conditions. That is, processing circuitry may use the in vivo transfer function to determine a delta value based on a pre-calibration value and a calibration value for one or more monitor electrodes, where processing circuitry measured the pre-calibration value for the one or more monitor electrodes when the one or more monitor electrodes were not inserted in a patient, and processing circuitry measured the calibration value after the one or more monitor electrodes had been inserted in a patient (subcutaneous).

In some examples, processing circuitry may measure an operating parameter of monitor electrodes 302a and 302b and determine changes from a previous measurement of the operating parameter of monitor electrodes 302a and 302b before or after installation of the glucose monitor. In examples where processing circuitry takes the measurement after installation and monitor electrodes are disposed on sensor flex 12 under the skin, processing circuitry may use an in vivo transfer function as described above.

FIG. 7 is a flowchart illustrating an example technique of the disclosure.

A system for measuring glucose levels of a patient more accurately may include a glucose monitor with one or more monitor electrodes and one or more working electrodes, and processing circuitry that measures one or more calibration values of an operating parameter (e.g., impedance, resistance, capacitance) of one or more monitor electrodes, wherein a first chemistry stack is disposed on at least one monitor electrode of the one or more monitor electrodes (702). Processing circuitry may measure the calibration value around the time the glucose monitor, or a new sensor flex, is installed on a patient. In some examples, the one or more monitor electrodes include a first monitor electrode and a second monitor electrode. In some examples the first and second monitor electrodes have the same chemistry stack, and in other examples the first and second monitor electrodes have a different chemistry stack. Processing circuitry may measure a calibration value for an operating parameter of each monitor electrode. For example, processing circuitry may measure a first calibration value of an operating parameter of the first monitor electrode; and a second calibration value of an operating parameter of the second monitor electrode. In some examples, processing circuitry may measure the calibration values for the same operating parameter on each monitor electrode (i.e., a first and second impedance corresponding to the first and second monitor electrodes). In some examples, processing circuitry may measure the calibration values for different operating parameters on each monitor electrode (i.e., a calibration value for the impedance of the first monitor electrode and a calibration value for the resistance of the second monitor electrode).

The one or more monitor electrodes may be positioned in various ways. In some examples, the monitor electrodes may be positioned on a sensor flex of the glucose monitor such that the monitor electrodes will be installed under the skin inside the patient. In some examples, the monitor electrodes may be positioned on a sensor flex of the glucose monitor such that the monitor electrodes will be positioned above the skin outside of the patient when the sensor flex is installed in the patient. In some examples, one or more monitor electrodes may be positioned under the skin, and one or more monitor electrodes may be positioned above the skin after installation.

Processing circuitry may also retrieve one or more pre-calibration values of the operating parameter of the one or more monitor electrodes, wherein the one or more pre-calibration values were measured before the calibration value (704). Processing circuitry may measure one or more pre-calibration values of the operating parameter of the one or more monitor electrodes around the time of the manufacture/assembly of the glucose monitor. Processing circuitry may store the one or more pre-calibration values in memory. Before installation of the glucose monitor on a patient, processing circuitry may retrieve the one or more pre-calibration values from memory. In some examples, the one or more pre-calibration values are stored in memory via an external source, for example data loaded onto the glucose monitor by the manufacturer or assembler.

In some examples, the glucose monitor includes a first monitor electrode with a first chemistry stack and a second monitor electrode with a second chemistry stack. Processing circuitry may retrieve a first pre-calibration value of an operating parameter of the first monitor electrode and a second pre-calibration value of an operating parameter of the second monitor electrode. In some examples, processing circuitry may retrieve a pre-calibration value of an operating parameter of each monitor electrode of the one or more monitor electrodes. In some examples, processing circuitry may retrieve the pre-calibration values for the same operating parameter on each monitor electrode (i.e., a first and second impedance corresponding to the first and second monitor electrodes). In some examples, processing circuitry may retrieve the pre-calibration values for different operating parameters on each monitor electrode (i.e., a pre-calibration value for the impedance of the first monitor electrode and a pre-calibration value for the resistance of the second monitor electrode).

Processing circuitry may retrieve a number of pre-calibration values equal to the number of measured calibration values, where each retrieved pre-calibration value corresponds to a measured calibration value. For example, a first measured calibration value may be for a first operating parameter of a first monitor electrode having a first chemistry stack, and a second measured calibration value may be for the first operating parameter of a second monitor electrode having the first chemistry stack, and a third measured calibration value may be for a second operating parameter of a third monitor electrode having a second chemistry stack. Correspondingly, a first retrieved pre-calibration value may be for a first operating parameter of a first monitor electrode having a first chemistry stack, and a second retrieved pre-calibration value may be for the first operating parameter of a second monitor electrode having the first chemistry stack, and a third retrieved pre-calibration value may be for a second operating parameter of a third monitor electrode having a second chemistry stack. In some examples, processing circuitry may only measure calibration values that will correspond to pre-calibration values in memory.

Processing circuitry determines one or more delta values using the one or more calibration values and the one or more pre-calibration values (706). For example, processing circuitry may subtract a first pre-calibration value from a first calibration value, or processing circuitry may divide a first pre-calibration value by a first calibration value to determine a first delta value.

Processing circuitry may determine a delta value for each pair of corresponding pre-calibration values and calibration values. For example, processing circuitry may determine a first delta value using a first pre-calibration value for a first operating parameter of a first monitor electrode having a first chemistry stack and using a first calibration value for the first operating parameter of the first monitor electrode having the first chemistry stack. Processing circuitry may also determine a second delta value using a second pre-calibration value for the first operating parameter of a second monitor electrode having a second chemistry stack and using a second calibration value for the first operating parameter of the second monitor electrode having the second chemistry stack.

In some examples, the one or more monitor electrodes may be inserted into a patient when the glucose monitor is installed on the patient, and processing circuitry may measure one or more in vivo calibration values for the one or more monitor electrodes. One or more corresponding pre-calibration values may not have been measured in vivo. To determine the one or more delta values, processing circuitry may generate an in vivo transfer function to account for changes in the operating parameter value based on in vivo conditions. Processing circuitry may determine the one or more delta values based on the one or more pre-calibration values, the one or more in vivo calibration values, and the in vivo transfer function.

Processing circuitry may calibrate glucose values sensed by the one or more working electrodes using the one or more delta values, wherein a chemistry stack is disposed on at least one working electrode of the one or more working electrodes (708).

Processing circuitry may translate the one or more delta values to a change in the operating parameter value of the one or more working electrodes. Using transfer functions or lookup tables, processing circuitry may determine a new calibration factor for the one or more working electrodes based on the one or more delta values for calibration values of the monitor electrodes. The new calibration factor for the working electrodes may differ from an old calibration factor for the working electrodes, where the old calibration factor was determined around the time of manufacture/assembly of glucose monitor 100. The change in calibration factor for the one or more working electrodes reflects a change in the measured operating parameter value of the one or more working electrodes when exposed to the same glucose levels. Processing circuitry may determine glucose values sensed by the one or more working electrodes based on the change in the measured operating parameter value. When processing circuitry determines glucose values based on the measured operating parameter value, processing circuitry may use the new calibration factor in the determination.

In some examples, the one or more working electrodes comprise a first working electrode and a second working electrode, where each working electrode has a different chemistry stack. In some examples the chemistry stacks of the one or more working electrodes are the same. Processing circuitry may calibrate glucose values sensed by the first working electrode and glucose values sensed by the second working electrode using the same one or more delta values. Processing circuitry may use a different lookup table or transfer function to determine a new calibration factor for the one or more working electrodes with different chemistry stacks based on the one or more delta values. For example, processing circuitry may use a first lookup table or transfer function to determine a new calibration factor for a first working electrode with a first chemistry stack based on a first delta value, and processing circuitry may use a second lookup table or transfer function to determine a new calibration factor for a second working electrode with a second chemistry stack based on the first delta value.

Processing circuitry may determine a new calibration factor for each of the one or more working electrodes for each of the one or more delta values. For example, processing circuitry may determine a first new calibration factor for a first working electrode based on a first delta value, and determine a second new calibration factor for the first working electrode based on a second delta value. Processing circuitry may take an average of all determined new calibration factors for each of the one or more working electrodes. Processing circuitry may use the average new calibration factor for a working electrode to calibrate the glucose levels sensed by that working electrode.

In one or more examples, the functions described may be implemented in hardware, software, firmware, or any combination thereof. If implemented in software, the functions may be stored on or transmitted over a computer-readable medium as one or more instructions or code, and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can include RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more DSPs, general purpose microprocessors, ASICs, FPGAs, or other equivalent integrated or discrete logic circuitry, as well as any combination of such components. Accordingly, the term "processor," as used herein may refer to any of the foregoing structures or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless communication device or wireless handset, a microprocessor, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A system for monitoring glucose, the system comprising:

a glucose monitor comprising one or more monitor electrodes and one or more working electrodes, wherein a first chemistry stack is disposed on at least one monitor electrode of the one or more monitor electrodes and a second chemistry stack is disposed on at least one working electrode of the one or more working electrodes, and wherein the first chemistry stack comprises materials that react more to aging or environmental effects relative to the second chemistry stack; and processing circuitry configured to:

measure one or more calibration values of an operating parameter of a first type of the one or more monitor electrodes;

retrieve one or more pre-calibration values of the operating parameter of the one or more monitor electrodes, wherein the one or more pre-calibration values were measured before the calibration values;

determine one or more delta values using the one or more calibration values and the one or more pre-calibration values, wherein the one or more delta values are indicative of a first reaction of the first chemistry stack of the at least one monitor electrode to the aging or environmental effects;

translate the one or more delta values associated with the operating parameter of the one or more monitor electrodes to a change in an operating parameter of a second type of the one or more working electrodes, wherein the first type and the second type are the same and wherein the change in the operating parameter of the second type is indicative of a second reaction of the second chemistry stack of the at least one working electrode to the aging or environmental effects, the first reaction being different from the second reaction, and wherein translating the one or more delta values comprises utilizing a relationship between the second reaction of the second chemistry stack and the first reaction of the first chemistry stack; and calibrate glucose values sensed by the one or more working electrodes based on the translation of the one or more delta values associated with the operating parameter of the one or more monitor electrodes to the change in the operating parameter of the one or more working electrodes.

2. The system of claim 1, wherein the one or more monitor electrodes comprise a first monitor electrode having the first chemistry stack and a second monitor electrode having a third chemistry stack, wherein to measure the one or more calibration values of the operating parameter of the one or more monitor electrodes, the processing circuitry is configured to:

measure a first calibration value of the operating parameter of the first monitor electrode; and measure a second calibration value of the operating parameter of the second monitor electrode, wherein to retrieve the one or more pre-calibration values of the operating parameter of the one or more monitor electrodes, the processing circuitry is configured to:

retrieve a first pre-calibration value of the operating parameter of the first monitor electrode having the first chemistry stack; and retrieve a second pre-calibration value of the operating parameter of the second monitor electrode having the third chemistry stack, wherein to determine the one or more delta values using the one or more calibration values and the one or more pre-calibration values, the processing circuitry is configured to:

determine a first delta value using the first calibration value and the first pre-calibration value; and determine a second delta value using the second calibration value and the second pre-calibration value, and wherein to calibrate the glucose values sensed by the one or more working electrodes using the one or more delta values, the processing circuitry is configured to calibrate the glucose values sensed by the one or more working electrodes using the first delta value and the second delta value.

3. The system of claim 1, wherein the one or more working electrodes comprise a first working electrode having the second chemistry stack and a second working electrode having a third chemistry stack, wherein the third chemistry stack is different from the second chemistry stack, and wherein the processing circuitry is configured to:

calibrate glucose values sensed by the first working electrode using a first delta value of the one or more delta values; and calibrate glucose values sensed by the second working electrode using the same first delta value of the one or more delta values.

4. The system of claim 1, wherein to translate the one or more delta values, the processing circuitry is configured to utilize a transfer function or a lookup table to determine new calibration factors for the one or more working electrodes based on the one or more delta values.

5. The system of claim 1, wherein to determine the one or more delta values, the processing circuitry is configured to:

generate an in vivo transfer function to account for changes in the operating parameter of the first type based on in vivo conditions.

6. The system of claim 1, wherein the glucose monitor further comprises a sensor flex, and wherein the one or more working electrodes and the one or more monitor electrodes are positioned on the sensor flex.

7. The system of claim 6, wherein the glucose monitor further comprises a circuit board, and wherein:

the circuit board is positioned on a first side of the sensor flex, and the one or more monitor electrodes are positioned on the same side of the sensor flex as the circuit board.

8. The system of claim 1, wherein the one or more monitor electrodes are positioned adjacent one another.

9. The system of claim 1, wherein at least one of the one or more monitor electrodes is positioned subcutaneously after the glucose monitor is installed on a patient.

10. The system of claim 1, wherein at least one of the one or more monitor electrodes is positioned adjacent at least one of the one or more working electrodes.

11. The system of claim 1, wherein at least one of the one or more monitor electrodes is configured to operate as a supplementary working electrode, reference electrode, or counter electrode.

12. A method of calibrating glucose values measured using a glucose monitor comprising one or more monitor electrodes and one or more working electrodes, wherein a first chemistry stack is disposed on at least one monitor electrode of the one or more monitor electrodes and a second chemistry stack is disposed on at least one working electrode of the one or more working electrodes, and wherein the first chemistry stack comprises materials that react more to aging or environmental effects relative to the second chemistry stack, the method comprising:

measuring one or more calibration values of an operating parameter of a first type of the one or more monitor electrodes;

retrieving one or more pre-calibration values of the operating parameter of the one or more monitor electrodes, wherein the one or more pre-calibration values were measured before the calibration values;

determining one or more delta values using the one or more calibration values and the one or more pre-calibration values, wherein the one or more delta values are indicative of a first reaction of the first chemistry stack of the at least one monitor electrode to the aging or environmental effects;

translating the one or more delta values associated with the operating parameter of the one or more monitor electrodes to a change in an operating parameter of a second type of one or more working electrodes, wherein the first type and the second type are the same and wherein the change in the operating parameter of the second type is indicative of a second reaction of the second chemistry stack of the at least one working electrode to the aging or environmental effects, the first reaction being different from the second reaction, and wherein translating the one or more delta values comprises utilizing a relationship between the second reaction of the second chemistry stack and the first reaction of the first chemistry stack; and calibrating glucose values sensed by the one or more working electrodes based on the translation of the one or more delta values associated with the operating parameter of the one or more monitor electrodes to the change in the operating parameter of the one or more working electrodes.

13. The method of claim 12, wherein the one or more monitor electrodes comprise a first monitor electrode having the first chemistry stack and a second monitor electrode having a third chemistry stack, wherein measuring the one or more calibration values of the operating parameter of one or more monitor electrodes comprises:

measuring a first calibration value of the operating parameter of the first monitor electrode; and measuring a second calibration value of the operating parameter of the second monitor electrode, wherein retrieving the one or more pre-calibration values of the operating parameter of the one or more monitor electrodes comprises:

retrieving a first pre-calibration value of the operating parameter of the first monitor electrode having the first chemistry stack; and retrieving a second pre-calibration value of the operating parameter of the second monitor electrode having the third chemistry stack, wherein determining the one or more delta values using the one or more calibration values and the one or more pre-calibration values comprises:

determining a first delta value using the first calibration value and the first pre-calibration value; and determining a second delta value using the second calibration value and the second pre-calibration value, and wherein calibrating the glucose values sensed by the one or more working electrodes using the one or more delta values comprises calibrating the glucose values sensed by the one or more working electrodes using the first delta value and the second delta value.

14. The method of claim 12, wherein the one or more working electrodes comprise a first working electrode having the second chemistry stack and a second working electrode having a third chemistry stack, wherein the third chemistry stack is different from the second chemistry stack, the method further comprising:

calibrating glucose values sensed by the first working electrode using a first delta value of the one or more delta values; and calibrating glucose values sensed by the second working electrode using the same first delta value of the one or more delta values.

15. The method of claim 12, wherein translating the one or more delta values comprises utilizing a transfer function or a lookup table to determine new calibration factors for the one or more working electrodes based on the one or more delta values.

16. The method of claim 12, wherein determining the one or more delta values comprises:

generating an in vivo transfer function to account for changes in the operating parameter of the first type based on in vivo conditions.

17. A glucose monitor comprising:

one or more working electrodes;

one or more monitor electrodes;

a first chemistry stack disposed on at least one monitor electrode of the one or more monitor electrodes, wherein the first chemistry stack has a first reaction to environmental conditions; and a second chemistry stack disposed on at least one working electrode of the one or more working electrodes, wherein the second chemistry stack has a second reaction to the environmental conditions, the second reaction being less than the first reaction, that can be determined based on a relationship between the second reaction and the first reaction based on a translation of a difference in calibration values of an operating parameter of a first type associated with the at least one monitor electrode to a corresponding difference of an operating parameter of a second type associated with the at least one working electrode, wherein the first type and the second type are the same.

18. The glucose monitor of claim 17, wherein:

the one or more monitor electrodes comprise a first monitor electrode and a second monitor electrode, the first chemistry stack having the first reaction is disposed on the first monitor electrode, a third chemistry stack is disposed on the second monitor electrode, wherein the third chemistry stack has a third reaction to the environmental conditions, and wherein the third chemistry stack is different from the first chemistry stack, and the second reaction can be determined based on one or more of the first reaction and the third reaction.

19. The glucose monitor of claim 17, wherein:

the one or more working electrodes comprise a first working electrode and a second working electrode, the second chemistry stack having the second reaction is disposed on the first working electrode, a third chemistry stack is disposed on the second working electrode, the third chemistry stack has a third reaction to the environmental conditions, and the third reaction can be determined based on the first reaction.

20. The glucose monitor of claim 17, further comprising processing circuitry configured to:

measure one or more calibration values of the operating parameter of the one or more monitor electrodes, wherein the one or more calibration values are measured after the first chemistry stack has the first reaction to the environmental conditions;

retrieve one or more pre-calibration values of the operating parameter of the one or more monitor electrodes, wherein the one or more pre-calibration values were measured before the first chemistry stack has the first reaction to the environmental conditions;

determine one or more delta values using the one or more calibration values and the one or more pre-calibration values; and determine the second reaction of the second chemistry stack to the environmental conditions using the one or more delta values.

* * * * *